United States Patent

Matsuo et al.

[11] Patent Number: 4,772,633
[45] Date of Patent: Sep. 20, 1988

[54] 6-PYRIDYL- AND 6-PHENYL-3-PHENYL-1-HEXENES AND -1-HEXYNES, COMPOSITION CONTAINING THEM, AND INSECTICIDAL AND ACARICIDAL METHOD OF USING THEM

[75] Inventors: Noritada Matsuo, Rochester, N.Y.; Kazunori Tsushima, Nishinomiya; Sumio Nishida, Takarazuka, both of Japan; Toshihiko Yano, Ikoma; Masachika Hirano, Osaka, both of Japan

[73] Assignee: Sumitomo Chemical Company, Limited, Osaka, Japan

[21] Appl. No.: 831,180

[22] Filed: Feb. 20, 1986

[51] Int. Cl.$^4$ .................. A01N 43/40; A01N 33/10; C07D 405/10; C07C 149/31
[52] U.S. Cl. .................. 514/717; 514/338; 514/345; 514/464; 514/466; 514/658; 514/713; 514/720; 514/749; 514/764; 546/270; 546/290; 546/301; 546/302; 546/303; 549/434; 549/440; 549/443; 549/445; 564/433; 568/49; 568/53; 568/56; 568/58; 568/635; 568/639; 570/128; 585/25
[58] Field of Search ............... 546/270, 290, 301, 302, 546/303; 568/56, 58, 631, 49, 53, 635, 639; 514/351, 711, 719, 338, 345, 464, 466, 658, 713, 717, 720, 749, 764; 549/434, 440, 443, 445; 564/433; 585/25; 570/128

[56] References Cited

U.S. PATENT DOCUMENTS 4,562,213 12/1985 Nishida et al. ............... 546/270

FOREIGN PATENT DOCUMENTS 3326180 1/1984 Fed. Rep. of Germany ...... 514/711
42339 3/1985 Japan ............................... 514/351
2120664 12/1983 United Kingdom ............... 514/351

Primary Examiner—Mary C. Lee
Assistant Examiner—Kurt G. Briscoe
Attorney, Agent, or Firm—Stevens, Davis, Miller & Mosher

[57] ABSTRACT

This invention relates to a novel compound represented by the following general formula (I), its production, and an insecticidal and acaricidal composition containing it as an active ingredient:

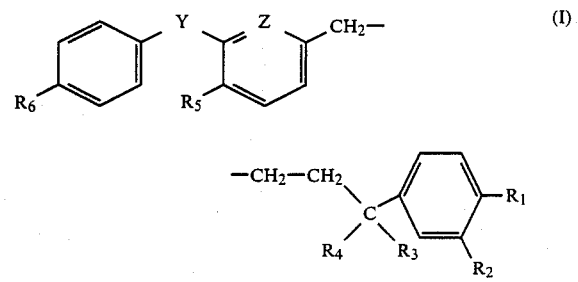

wherein $R_1$ and $R_2$, which may be the same or different, are a hydrogen atom, a halogen atom, a lower alkyl group, a trifluoromethyl group, a lower alkoxyl group, a lower alkenyloxy group or a halogenated lower alkoxyl group or are, taken together, a methylenedioxy group; $R_3$ is a vinyl group or a ethynyl group; $R_4$ is a hydrogen atom or a lower alkyl group; $R_5$ is a hydrogen atom or a fluorine atom; $R_6$ is a hydrogen atom, a halogen atom, a lower alkyl group, a lower alkoxyl group or a trifluoromethyl group; Z is a nitrogen atom or a group represented by the formula —CH=; when Z is a nitrogen atom, Y is an oxygen atom; and when Z is a group of the formula —CH=, Y is an oxygen atom, a sulfur atom, a methylene group or a group represented by the formula —NH—.

27 Claims, No Drawings

6-PYRIDYL- AND 6-PHENYL-3-PHENYL-1-HEXENES AND -1-HEXYNES, COMPOSITION CONTAINING THEM, AND INSECTICIDAL AND ACARICIDAL METHOD OF USING THEM

The present invention relates to a novel compound, its production and an insecticidal and acaricidal composition containing it as an active ingredient.

The present inventors extensively studied to develop a compound having excellent insecticidal and acaricidal activities, and as a result, found that a novel compound represented by the following general formula (I) (hereinafter referred to as present compound) is superior in the insecticidal and acaricidal activities as well as very low in toxicity to fishes. The present inventors thus attained to the present invention.

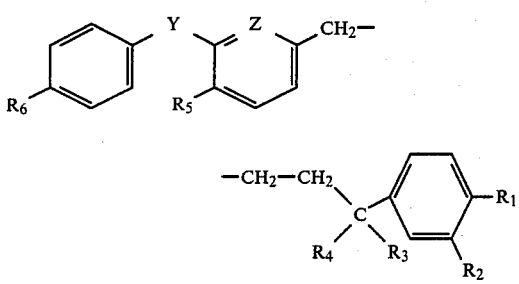

In this formula, $R1_1$ and $R_2$, which may be the same or different, are a hydrogen atom, a halogen atom (e.g. fluorine, chlorine, bromine), a lower alkyl group (e.g. $C_1$–$C_5$ alkyl), a trifluoromethyl group, a lower alkoxyl group (e.g. $C_1$–$C_5$ alkoxy), a lower alkenyloxy group (e.g. $C_2$–$C_5$ alkenyloxy) or a halogenated lower alkoxyl group (e.g. fluOrinated or chlorinated $C_1$–$C_5$ alkoxy), or, taken together, a methylenedioxy group; $R_3$ is a vinyl or ethynyl group; $R_4$ is a hydrogen atom or a lower alkyl group (e.g. $C_1$–$C_5$ alkyl); $R_5$ is a hydrogen or fluorine atom; $R_6$ is a hydrogen atom or a halogen atom (e.g. fluorine, chlorine, bromine), a lower alkyl group (e.g. $C_1$–$C_5$ alkyl), a lower alkoxyl group (e.g. $C_1$–$C_5$ alkoxy) or trifluoromethyl group; Z is a nitrogen atom or a group represented by the formula —CH=; when Z is a nitrogen atom, Y is an oxygen atom, and when Z is a group of the formula —CH=, Y is an oxygen or sulfur atom, a methylene group or a group represented by the formula —NH—.

Of the present compounds represented by the foregoing general formula (I), preferred compounds are such that $R_1$ and $R_2$, which may be the same or different, are a hydrogen or halogen atom, or a $C_1$–$C_4$ alkyl, trifluoromethyl, $C_1$–$C_4$ alkoxyl, $C_2$–$C_4$ alkenyloxy or halogenated $C_1$–$C_4$ alkoxyl group, or, taken tOgether, a methylenedioxy group; $R_4$ is a $C_1$–$C_4$ alkyl group; $R_6$ is a hydrogen or halogen atom, or a $C_1$–$C_4$ alkyl, $C_1$–$C_4$ alkoxyl or trifluoromethyl group; Z is a group represented by the formula —CH=; and Y is an oxygen atom or a group represented by the formula —NH—. More preferred compounds are such that, in the foregoing preferred compounds, $R_3$ is an ethynyl group and $R_4$ is a methyl group.

Specific examples of insect pests to which the present compounds are particularly effective include Hemiptera such as planthoppers, leafhoppers, aphids, bugs, whiteflies, etc., Lepidoptera such as diamond-back moth (*Plutella xylostella*), rice stem borer (*Chilo suppres-salis*), rice leafroller (*Cnaphalocrocis medinalis*), armyworms and cutworms, etc., Diptera such as common mosquito (*Culex pipiens pallens*), housefly (*Musca domestica*), etc., Dictyoptera such as German cockroach (*Blattella germanica*), etc., Coleoptera, Orthoptera and mites such as carmine spider mite (*Tetranychus cinnabarinus*), citrus red mite (*Panonychus citri*), etc. The term "an insecticidal and acaricidal composition" referred to hereinafter includes any composition which comprises the present compound as an active ingredient and is capable of controlling and/or killing insects and/or mites as mentioned above.

The present compounds can be produced, for example, by the following methods.

Method 1:

The present compound represented by the general formula (VI) which corresponds to the present compound of the general formula (I) wherein $R_3$ is a vinyl group,

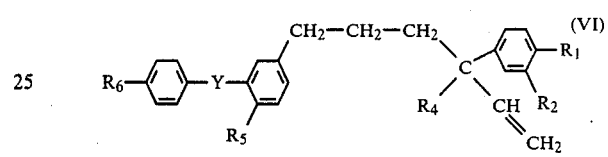

wherein $R_1$, $R_2$, $R_4$, $R_5$, $R_6$ and Y have the same meanings as described above, can be obtained (1) by reacting a compound represented by the general formula (II),

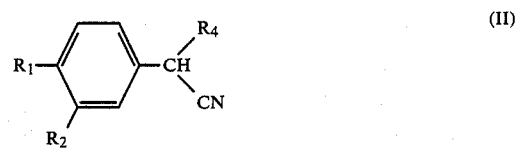

wherein $R_1$, $R_2$ and $R_4$ have the same meanings as described above, with a compound represented by the general formula (III),

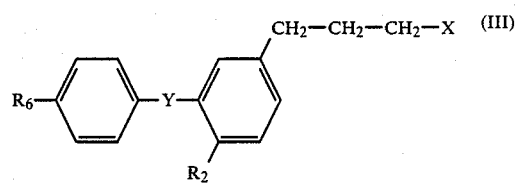

wherein $R_5$, $R_6$ and Y have the same meanings as described above, and X represents a halogen atom or a tosyloxy or mesyloxy group, for example, in dimethylformamide in the presence of sodium hydride to obtain a nitrile compound represented by the general formula (IV),

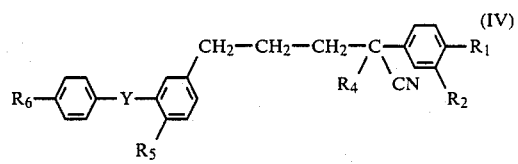

wherein $R_1$, $R_2$, $R_4$, $R_5$, $R_6$ and Y have the same meanings as described above, (2) reacting said nitrile compound with a reducing agent (e.g. diisobutylaluminum hydride) to obtain an aldehyde compound represented by the general formula (V),

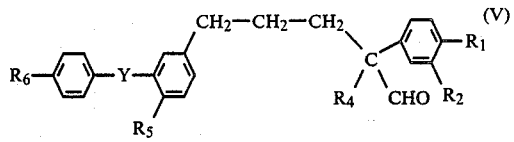

wherein $R_1$, $R_2$, $R_4$, $R_5$, $R_6$ and Y have the same meanings as described above, (3) and then reacting said aldehyde compound with an ylide compound represented by the formula,

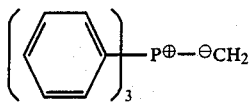

[which is prepared from methyl triphenylphosphonium halide represented by the formula,

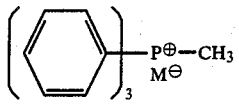

wherein M represents a halogen atom, and a base (e.g. n-butyl lithium, sec-butyl lithium, phenyl lithium)]

according to the Wittig, reaction (refer to Org. Reaction, Vol. 14, pp. 2570–490) to introduce a vinyl group.

Also, the present compound represented by the general formula (VII), which corresponds to the present compound of the general formula (I) wherein $R_3$ is an ethynyl group, can be obtained by reacting said aldehyde compound (V) with a Wittig reagent for introduction of a dihalomethylene group prepared from, for example, carbon tetrabromide or carbon tetrachloride and triphenyl phosphine, trialkyl phosphine or hexamethylphosphoroustriamide, according to the Wittig reaction (refer to Org. Reaction, Vol. 14, pp. 270–490) to introduce a dihalovinyl group, and then treating the resulting compound with a base. This reaction is expressed as follows:

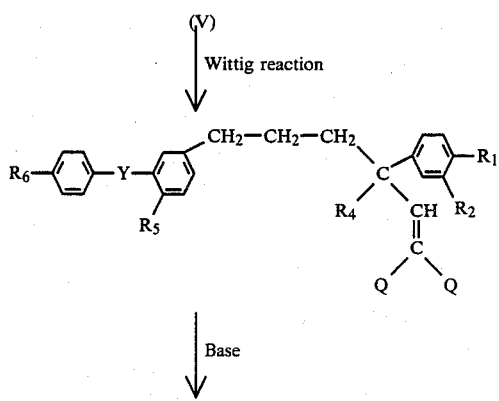

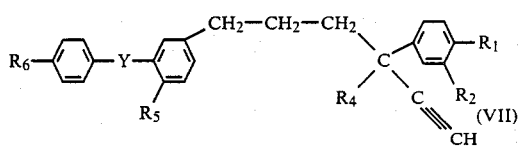

wherein $R_1$, $R_2$, $R_4$, $R_5$, $R_6$ and Y have the same meanings as described above, and Q is a bromine or chlorine atom.

Method 2:

First, a nitrile compound represented by the general formula (XV),

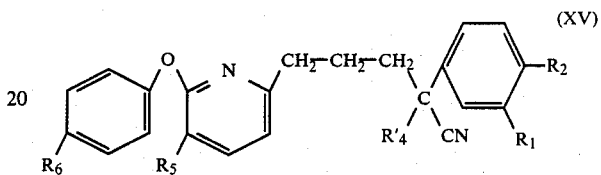

wherein $R_1$, $R_2$, $R_5$ and $R_6$ have the same meanings as described above, and $R'_4$ represents a lower alkyl group, is produced, (1) by reacting a compound represented by the general formula (VIII),

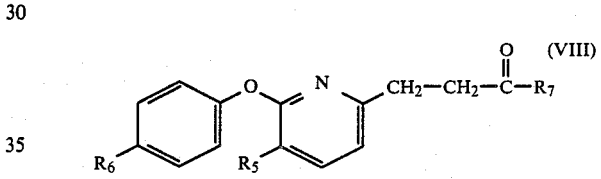

wherein $R_5$ and $R_6$ have the same meanings as described above, and $R_7$ represents a lower alkoxyl group, with a compound represented by the general formula (IX),

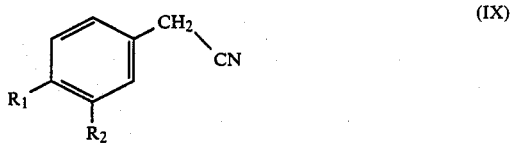

wherein $R_1$ and $R_2$ have the same meanings as described above, for example, in tetrahydrofuran in the presence of sodium hydride to obtain a compound represented by the general formula (X),

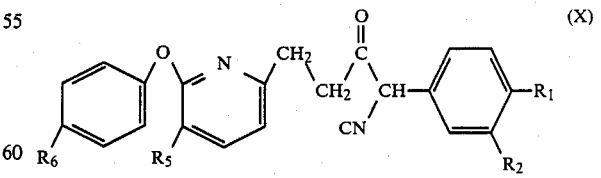

wherein $R_1$, $R_2$, $R_5$ and $R_6$ have the same meanings as described above, (2) reacting said compound (X) with a reducing agent (e.g. sodium borohydride), for example, in ethanol to obtain an alcohol compound represented by the general formula (XI),

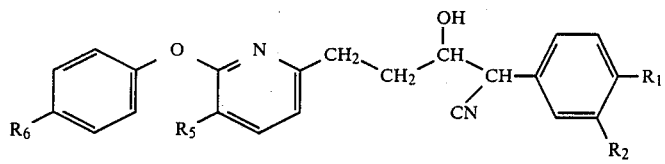

wherein $R_1$, $R_2$, $R_5$, and $R_6$ have the same meanings as described above, (3) reacting said alcohol compound (XI) with methanesulfonyl chloride in the presence of a base [e.g. 1,8-diazabicyclo[5,4,0]undec-7-ene(DBU)]or subjecting said alcohol compound (XI) to a reaction with other reagent for dehydration to obtain a compound represented by the general formula (XII),

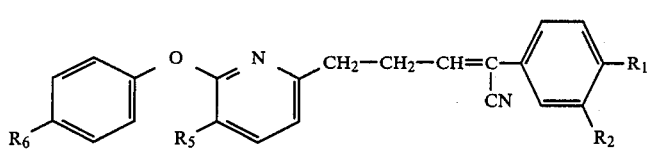

wherein $R_1$, $R_2$, $R_5$ and $R_6$ have the same meanings as described above, (4) reducing said compound (XII) with hydrogen gas, for example, in the presence of a noble metal catalyst (e.g. palladium-carbon powder), that is, subjecting said compound (XII) to catalytic hydrogenation, to obtain a compound represented by the general formula (XIII),

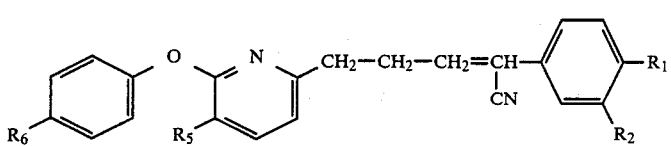

wherein $R_1$, $R_2$, $R_5$ and $R_6$ have the same meaning as described above, (5) and then reacting said compound (XIII) with a compound represented by the general formula (XIV), $$R'_4 X' \quad \text{(XIV)}$$

wherein $R'_4$ has the same meaning as described above, and $X'$ represents a halogen atom, either as such or, if necessary, for example in dry dimethylformamide in the presence of sodium hydride. Thereafter, the resulting nitrile compound represented by the general formula (XV) can be converted to the present compound of the general formula (XVI) [which corresponds to the present compound of the general formula (I) wherein $R_3$ is a vinyl group]and the present compound of the general formula (XVII) [which corresponds to the present compound of the general formula (I) wherein $R_3$ is an ethynyl group]in the same manner as in the nitrile compound of the general formula (IV) of Method 1.

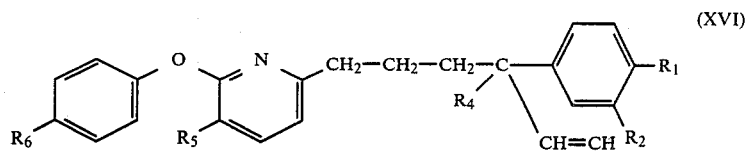

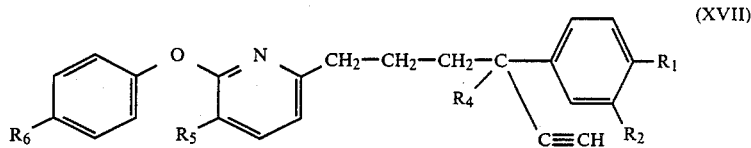

In the above formulae, $R_1$, $R_2$, $R_4$, $R_5$ and $R_6$ have the same meanings as described above.

Method 3:

The present compound of the general formula (I) wherein $R_3$ is an ethynyl group, and, at least one of $R_1$ and $R_2$ is a lower alkoxyl group, a lower alkenyloxy group or a halogenated lower alkoxyl group can be obtained.

(1) by reacting the dihalovinyl intermediate in the procedures described in Methods 1 and 2, which is represented by the general formula

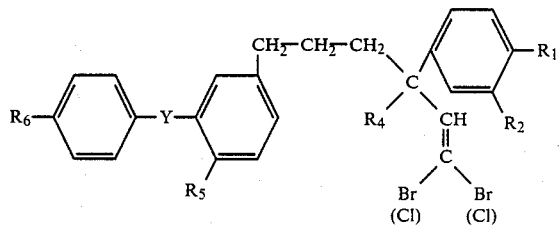

or

-continued

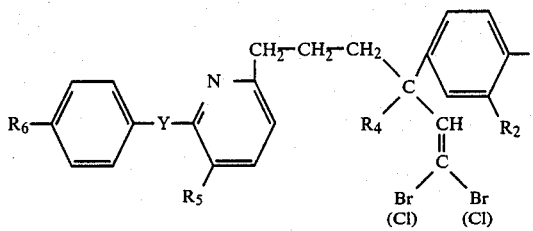

wherein at least one of $R_1$ and $R_2$ is a methoxy group, with a reagent for removing the methoxy group to lead to the corresponding hydroxyl compound (compound wherein at least one of $R_1$ and $R_2$ is a hydroxyl group), (2) reacting said hydroxyl compound with a base to convert the dihalovinyl group in the compound into ethynyl group, (3) and then reacting the resulting compound with a halide represented by the general formula $$R'_1X'$$

wherein $R'_1$ represents a lower alkyl, lower alkenyl or halogenated lower alkyl group, and $X'$ represents a halogen atom (e.g. chlorine, bromine) in the presence of a base (e.g. sodium hydride, potassium hydride, n-butyl lithium, potassium tert-butoxide, sodium hydroxide, potassium hydroxide).

Examples of the present compounds which can be produced by the foregoing methods will be shown below.

3-(4-Chlorophenyl)-3-methyl-6-{3-(4-bromophenoxy)-4 fluorophenyl}-1-hexyne
3-(4-Ethoxyphenyl)-3-ethyl-6-{3-(4-chlorophenoxy)-4-fluorophenyl}-1-hexyne
3-(4-Ethoxyphenyl)-3-methyl-6-{3-(4-tertbutylphenoxy)-4-fluorophenyl}-1-hexyne
3-(4-Ethoxyphenyl)-3-ethyl-6-{3-(4-trifluoromethylphenoxy)-4-fluorophenyl}-1-hexyne
3-(3,4-Dichlorophenyl)-3-methyl-6-{(3-(4-fluorophenoxy)-4-fluorophenyl}-1-hexyne
3-(4-tert-Butylphenyl)-3-methyl-6-{(3-(4-fluorophenoxy)-4-fluorophenyl}-1-hexyne
3-(4-Difluoromethoxyphenyl)-3-methyl-6-{3-(4-methylphenoxy)-4-fluorophenyl}-1-hexyne
3-(4-Difluoromethoxyphenyl)-3-methyl-6-{3-(4-fluorophenoxy)-4-fluorophenyl}-1-hexene
3-(4-Allyloxyphenyl)-3-methyl 6-{3-(4-fluorophenoxy)-4-fluorophenyl}-1-hexyne
3-(4-Ethoxyphenyl)-3-ethyl-6-(3-benzylphenyl)-1-hexyne
3-(4-Ethoxyphenyl)-6-(3-benzylphenyl)-1-hexyne
3-(4-Ethoxyphenyl)-6-(3-benzylphenyl)-1-hexene
3-(4-iso-propyloxyphenyl)-3-methyl-6-(3-benzylphenyl)-1-hexyne
3-(4-Trifluoromethylphenyl)-3-methyl-6-(3-benzyl-4-fluorophenyl)-1-hexyne
3-(4-Allyloxyphenyl)-3-methyl-6-(3-benzyl-4-fluorophenyl)-1-hexyne
3-(4-Difluoromethoxyphenyl)-3-methyl-6-(3-benzyl-4-fluorophenyl)-1-hexyne
3-(3,4-Methylenedioxyphenyl)-3-methyl-6-(3-benzyl-4-fluorophenyl)-1-hexyne
3-(4-Allyloxyphenyl)-3-n-propyl-6-(6-phenoxypyridin-2-yl)-1-hexyne
3-(4-Difluoromethoxyphenyl)-3-methyl-6-(6-phenoxypyridin-2-yl)-1-hexene
3-(4-Difluoromethoxyphenyl)-3-methyl-6-(6-phenoxypyridin-2-yl)-1-hexyne
3-(4-Difluoromethoxyphenyl)-3-ethyl-6-(6-phenoxypyridin-2-yl)-1-hexyne
3-(4-Difluoromethoxyphenyl)-3-n-propyl-6-(6-phenoxypyridin-2-yl)-1-hexyne
3-(4-Difluoromethoxyphenyl)-3-methyl-6-{3-(4-chlorophenoxy)-phenyl}-1-hexene
3-(4-Difluoromethoxyphenyl)-3-methyl-6-{3-(4-chlorophenoxy)-phenyl}-1-hexyne
3-(4-Difluoromethoxyphenyl)-3-methyl-6-{3-(4-fluorophenoxy)-phenyl}-1-hexyne
3-(4-Allyloxyphenyl)-3-methyl-6-{3-(4-methylphenoxy)-phenyl}-1-hexyne
3-(3,4-Methylenedioxyphenyl)-3-methyl-6-{3-(4-fluorophenoxy)-phenyl}-1-hexyne
3-(3,4-Methylenedioxyphenyl)-3-methyl-6-{3-(4-chlorophenoxy)-phenyl}-1-hexyne
3-(3-Chloro-4-ethoxyphenyl)-3-methyl-6-{3-(4-fluorophenoxy)-phenyl}-1-hexyne
3-(3-Chloro-4-fluorophenyl)-3-methyl-6-{3-(4-chlorophenoxy)-phenyl)}-1-hexyne
3-(3-Chloro-4-methoxyphenyl)-3-methyl-6-{3-(4-methylphenoxy)-phenyl}-1-hexyne
3-(4-Chlorophenyl)-3-methyl-6-(3-phenoxyphenyl)-1-hexene
3-(4-Chlorophenyl)-3-methyl-6-(3-phenoxyphenyl)-1-hexyne
3-(4-Chlorophenyl)-3-ethyl-6-(3-phenoxyphenyl)-1-hexene
3-(4-Chlorophenyl)-3-ethyl-6-(3-phenoxyphenyl)-1-hexyne
3-(4-Fluorophenyl)-3-methyl-6-(3-phenoxyphenyl)-1-hexene
3-(4-Fluorophenyl)-3-methyl-6-(3-phenoxyphenyl)-1-hexyne
3-(4-Fluorophenyl)-3-ethyl-6-(3-phenoxyphenyl)-1-hexene
3-(4-Fluorophenyl)-3-ethyl-6-(3-phenoxyphenyl)-1-hexyne
3-(4-Chlorophenyl)-3-n-propyl-6-(3-phenoxyphenyl)-1-hexyne
3-(4-Chlorophenyl)-3-methyl-6-(3-phenylthiophenyl)-1-hexyne
3-(4-Fluorophenyl)-3-methyl-6-(3-phenylthiophenyl)-1-hexyne
3-(4-Chlorophenyl)-3-methyl-6-(4-fluoro-3-phenylthiophenyl)-1-hexyne
3-(4-Fluorophenyl)-3-methyl-6-(4-fluoro-3-phenylthiophenyl)-1-hexyne
3-(4-Fluorophenyl)-3-methyl-6-{4-fluoro-3-(4-fluorophenylthio)phenyl}-1-hexyne
3-(4-Fluorophenyl)-3-methyl-6-{4-fluoro-3-(4-fluorophenylthio)phenyl}-1-hexene
3-(4-Fluorophenyl)-3-methyl-6-{3-(4-fluorobenzyl)-4-fluorophenyl)}-1-hexyne
3-(4-Allyloxyphenyl)-3-n-propyl-6-(3-phenoxyphenyl)-1-hexyne
3-(4-Difluoromethoxyphenyl)-3-methyl-6-(3-phenoxyphenyl)-1-hexene
3-(4-Difluoromethoxyphenyl)-3-methyl-6-(3-phenoxyphenyl)-1-hexyne
3-(4-Difluoromethoxyphenyl)-3-ethyl-6-(3-phenoxyphenyl)-1-hexene
3-(4-Difluoromethoxyphenyl)-3-ethyl-6-(3-phenoxyphenyl)-1-hexyne 3-(4-Difluoromethoxyphenyl)-6-(3-phenoxyphenyl)-1-hexene
3-(4-Difluoromethoxyphenyl)-6-(3-phenoxyphenyl)-1-hexyne
3-(4-Difluoromethoxyphenyl)-3-n-propyl-6-(3-phenoxyphenyl)-1-hexene
3-(4-Difluoromethoxyphenyl)-3-n-propyl-6-(3-phenoxyphenyl)-1-hexyne
3-(4-n Butyloxyphenyl)-3-ethyl-6-(3-phenoxyphenyl)-1-hexyne
3-(4-n-Butyloxyphenyl)-3-methyl-6-(3-phenoxyphenyl)-1-hexene
3-(4-n-Butyloxyphenyl)-3-methyl-6-(3-phenoxyphenyl)-1-hexyne
3-(4-n-Butyloxyphenyl)-6-(3-phenoxyphenyl)-1-hexene
3-(4-n-Butyloxyphenyl)-6-(3-phenoxyphenyl)-1-hexyne
3-(4-iso-Butyloxyphenyl)-3-methyl-6-(3-phenoxyphenyl)-1-hexene
3-(4-iso-Butyloxyphenyl)-3-methyl-6-(3-phenoxyphenyl)-1-hexyne
3-(4-Methoxyphenyl)-3-methyl-6-(3-phenoxyphenyl)-1-hexene
3-(4-Methoxyphenyl)-3-methyl-6-(3-phenoxyphenyl)-1-hexyne
3-(4-Ethoxyphenyl)-3-methyl-6-(3-phenoxyphenyl)-1-hexene
3-(4-Ethoxyphenyl)-3-methyl-6-(3-phenoxyphenyl)-1-hexyne
3-(4-Ethoxyphenyl)-3-ethyl-6-(3-phenoxyphenyl)-1-hexene
3-(4-Ethoxyphenyl)-3-ethyl-6-(3-phenoxyphenyl)-1-hexyne
3-(4-Ethoxyphenyl)-6-(3-phenoxyphenyl)-1-hexene
3-(4-Ethoxyphenyl)-6-(3-phenoxyphenyl)-1-hexyne
3-(4-Ethoxyphenyl)-3-n-butyl-6-(3-phenoxyphenyl)-1-hexene
3-(4-Fluorophenyl)-3-ethyl-6-(6-phenoxypyridin-2-yl)-1-hexene
3-(4-Fluorophenyl)-6-(6-phenoxypyridin-2-yl)-1-hexyne
3-(4-Fluorophenyl)-6-(6-phenoxypyridin-2-yl)-1-hexene
3-(4-Ethylphenyl)-3-methyl-6-(6-phenoxypyridin-2yl)-1-hexyne
3-(4-iso-Propylphenyl)-3-methyl-6-(6-phenoxypyridin-2-yl)-1-hexene
3-(4-Chlorophenyl)-3-methyl-6-(4-fluoro-6-phenoxypyridin-2-yl)-1-hexyne
3-(4-Fluorophenyl)-3-methyl-6-(4-fluoro-6-phenoxypyridin-2-yl)-1-hexyne
3-(4-Fluorophenyl)-3-methyl-6-(4-fluoro-6-phenoxypyridin-2-yl)-1-hexene
3-(4-Methoxyphenyl)-3-methyl-6-(4-fluoro-6-phenoxypyridin-2-yl)-1-hexyne
3-(3-Chloro-4-fluorophenyl)-3-methyl-6-(3-anilino-4-fluorophenyl)-1-hexene
3-(3-Chloro-4-fluorophenyl)-3-ethyl-6-(3-anilino-4-fluorophenyl)-1-hexyne
3-(3-Fluoro-4-chlorophenyl)-3-methyl-6-(3-anilino-4-fluorophenyl)-1-hexyne
3-(3-Chloro-4-ethoxyphenyl)-3-methyl-6-(3-anilino-4-fluorophenyl)-1-hexene
3-(3-Chloro-4-ethoxyphenyl)-3-methyl-6-(3-anilino-4-fluorophenyl)-1-hexyne
3-(3-Chloro-4-ethoxyphenyl)-3-ethyl-6-(3-anilino-4-fluorophenyl)-1-hexyne
3-(3-Chloro-4-ethoxyphenyl)-6-(3-anilino-4-fluorophenyl)-1-hexene
3-(3-Chloro-4-ethoxyphenyl)-6-(3-anilino-4-fluorophenyl)-1-hexyne
3-(3,4-Dichlorophenyl)-3-methyl-6-(3-anilino-4-fluorophenyl)-1-hexyne
3-(3,4-Methylenedioxyphenyl)-3-ethyl-6-(6-phenoxypyridin-2-yl)-1-hexyne
3-(3,4-Methylenedioxyphenyl)-3-n-propyl-6-(6-phenoxypyridin-2-yl)-1-hexyne
3-(3,4-Dichlorophenyl)-3-methyl-6-(6-phenoxypyridin-2-yl)-1-hexyne
3-(3-Chloro-4-fluorophenyl)-3-methyl-6-(6-phenoxypyridin-2-yl)-1-hexyne
3-(3-Chloro-4-ethoxyphenyl)-3-methyl-6-(6-phenoxypyridin-2-yl)-1-hexyne
3-(4-iso-Propyloxyphenyl)-3-methyl-6-(6-phenoxypyridin-2-yl)-1-hexene
3-(4-iso-Propyloxyphenyl)-3-ethyl-6-(6-phenoxypyridin-2-yl)-1-hexyne
3-(4-n-Propyloxyphenyl)-3-methyl-6-(6-phenoxypyridin-2-yl)-1-hexyne
3-(4-n-Propyloxyphenyl)-3-methyl-6-(6-phenoxypyridin-2-yl)-1-hexene
3-(4-Allyloxyphenyl)-3-methyl-6-(6-phenoxypyridin-2-yl)-1-hexene
3-(4-Chlorophenyl)-3-methyl-6-{3-(4-fluorophenoxy)phenyl}-1-hexene
3-(4-Chlorophenyl)-3-methyl-6-{3-(4-fluorophenoxy)phenyl}-1-hexyne
3-(4-Fluorophenyl)-3-methyl-6-{3-(4-fluorophenoxy)phenyl}-1-hexyne
3-(4-Fluorophenyl)-3-methyl-6-{3-(4-methylphenoxy)phenyl}-1-hexene
3-(4-Fluorophenyl)-3-methyl-6-{3-(4-methylphenoxy)phenyl}-1-hexyne
3-(4-Ethoxyphenyl)-3-methyl-6-{3-(4-fluorophenoxy)phenyl}-1-hexene
3-(4-Ethoxyphenyl)-3-methyl-6-{3-(4-fluorophenoxy)phenyl}-1-hexyne
3-(4-Ethoxyphenyl)-3-ethyl-6-{3-(4-fluorophenoxy)phenyl}-1-hexyne
3-(4-Ethoxyphenyl)-3-methyl-6-{3-(4-methylphenoxy)phenyl}-1-hexyne
3-(4-Trifluoromethylphenyl)-3-methyl-6-(3-phenylthiophenyl)-1-hexene
3-(4-Difluoromethoxyphenyl)-3-methyl-6-(3-phenylthiophenyl)-1-hexyne
3-(4-Trifluoromethylphenyl)-3-methyl-6-(4-fluoro-3-phenylthiophenyl)-1-hexyne
3-(4-Difluoromethoxyphenyl)-3-methyl-6-(4-fluoro-3-phenylthiophenyl)-1-hexyne
3-(4-Trifluoromethylphenyl)-3-methyl-6-{4-fluoro-3-(4-fluorophenylthio)phenyl}-1-hexyne
3-(4-Difluoromethoxyphenyl)-3-methyl-6-{4-fluoro-3-(4-fluorophenylthio)phenyl}-1-hexyne
3-(4-Trifluoromethylphenyl)-3-methyl-6-{3-(4-fluorobenzyl)-4-fluorophenyl}-1-hexyne
3-(4-Difluoromethoxyphenyl)-3-methyl-6-{3-(4-fluorobenzyl)-4-fluorophenyl}-1-hexyne
3-(3,4-Methylenedioxyphenyl)-3-methyl-6-(3-benzylphenyl)-1-hexyne
3-(3,4-Methylenedioxyphenyl)-3-methyl-6-(3-benzylphenyl)-1-hexene
3-(3-Chloro-4-ethoxyphenyl)-3-methyl-6-(3-benzylphenyl)-1-hexyne
3-(3-Chloro-4-fluorophenyl)-3-methyl-6-(3-benzylphenyl)-1-hexyne
3-(3,4-Methylenedioxyphenyl)-3-n-propyl-6-(3-phenoxyphenyl)-1-hexene 3-(3,4-Methylenedioxyphenyl)-3-n-propyl-6-(3-phenoxyphenyl)-1-hexyne
3-(3,4-Methylenedioxyphenyl)-3-methyl-6-(3-phenoxyphenyl)-1-hexene
3-(3,4-Methylenedioxyphenyl)-3-methyl-6-(3-phenoxyphenyl)-1-hexyne
3-(3,4-Methylenedioxyphenyl)-3-ethyl-6-(3-phenoxyphenyl)-1-hexene
3-(3,4-Methylenedioxyphenyl)-3-ethyl-6-(3-phenoxyphenyl)-1-hexyne
3-(3,4-Methylenedioxyphenyl)-6-(3-phenoxyphenyl)-1-hexene
3-(3,4-Methylenedioxyphenyl)-6-(3-phenoxyphenyl)-1-hexyne
3-(4-Ethoxyphenyl)-3-n-butyl-6-(3-phenoxyphenyl)-1-hexyne
3-(4-Ethoxyphenyl)-3-n-propyl-6-(3-phenoxyphenyl)-1-hexene
3-(4-Ethoxyphenyl)-3-n-propyl-6-(3-phenoxyphenyl)-1-hexyne
3-(4-Ethoxyphenyl)-3-iso-propyl-6-(3-phenoxyphenyl)-1-hexene
3-(4-Ethoxyphenyl)-3-iso-propyl-6-(3-phenoxyphenyl)-1-hexyne
3-(4-n-Propyloxyphenyl)-3-methyl-6-(3-phenoxyphenyl)-1-hexene
3-(4-n-Propyloxyphenyl)-3-methyl-6-(3-phenoxyphenyl)-1-hexyne
3-(4-iso-Propyloxyphenyl)-3-methyl-6-(3-phenoxyphenyl)-1-hexene
3-(4-iso-Propyloxyphenyl)-3-methyl-6-(3-phenoxyphenyl)-1-hexyne
3-(4-Methylphenyl)-3-methyl-6-(3-phenoxyphenyl)-1-hexene
3-(4-Methylphenyl)-3-methyl-6-(3-phenoxyphenyl)-1-hexyne
3-(4-Ethylphenyl)-3-methyl-6-(3-phenoxyphenyl)-1-hexyne
3-(4-n-Propylphenyl)-3-methyl-6-(3-phenoxyphenyl)-1-hexyne
3-(4-tert-Butylphenyl)-3-methyl-6-(3-phenoxyphenyl)-1-hexyne
3-(4-n-Butylphenyl)-3-methyl-6-(3-phenoxyphenyl)-1-hexyne
3-(4-iso-Proylphenyl)-3-methyl-6-(3-phenoxyphenyl)-1-hexyne
3-(4-Methylphenyl)-3-ethyl-6-(3-phenoxyhenyl)-1-hexene
3-(4-Methylphenyl)-3-ethyl-6-(3-phenoxyhenyl)-1-hexyne
3-(4-Difluoromethoxyphenyl)-3-methyl-6-{3-(4-chlorophenoxy)-4-fluorophenyl}-1-hexene
3-(4-Difluoromethoxyphenyl)-3-methyl-6-{3-(4-chlorophenoxy)-4-fluorophenyl}-1-hexyne
3-(4-Difluormethoxyphenyl)-3-methyl-6-{3-(4-fluorophenoxy)-4-fluorophenyl}-1-hexyne
3-(4-Allyloxyphenyl)-3-methyl-6-{3-(4-methylphenoxy)-4-fluorophenyl}-1-hexyne
3-(3,4-Methylenedioxyphenyl)-3-methyl-6-{3-(4-fluorophenoxy)-4-fluorophenyl}-1-hexyne
3-(3,4-Methylenedioxyphenyl)-3-methyl-6-{3-(4-chlorophenoxy)-4-fluorophenyl}-1-hexyne
3-(3-Chloro-4-ethoxyphenyl)-3-methyl-6-{3-(4-fluorophenoxy)-4-fluorophenyl}-1-hexyne
3-(3-Chloro-4-fluorophenyl)-3-methyl-6-{3-(4-chlorophenoxy)-4-fluorophenyl}-1-hexyne
3-(3-Chloro-4-methoxyphenyl)-3-methyl-6-{3-(4-methylphenoxy)-4-fluorophenyl}-1-hexyne
3-(4-n-Propyloxyphenyl)-3-methyl-6-(3-anilino-4-fluorophenyl)-1-hexyne
3-(4-Allyloxyphenyl)-3-methyl-6-(3-anilino-4-fluorophenyl)-1-hexene
3-(4-Allyloxyphenyl)-3-methyl-6-(3-anilino-4-fluorophenyl)-1-hexyne
3-(4-Allyloxyphenyl)-3-ethyl-6-(3-anilino-4-fluorophenyl)-1-hexyne
3-(4-Allyloxyphenyl)-6-(3-anilino-4-fluorophenyl)-1-hexene
3-(4-Allyloxyphenyl)-6-(3-anilino-4-fluorophenyl)-1-hexyne
3-(4-Allyloxyphenyl)-3-n-propyl-6-(3-anilino-4-fluorophenyl)-1-hexyne
3-(4-Allyloxyphenyl)-3-iso-propyl-6-(3-anilino-4-fluorophenyl)-1-hexyne
3-(4-Difluoromethyxyphenyl)-3-methyl-6-(3-anilino-4-flurophenyl)-1-hexene
3-(4-Difluoromethyoxyphenyl)-6-(6-phenoxypyridin-2-yl)-1-hexene
3-(4-Difluoromethyoxyphenyl)-6-(6-phenoxypyridin-2-yl)-1-hexyne
3-(3,4-Methylenedioxyphenyl)-3-methyl-6-(6-phenoxypyridin-2-yl)-1-hexene
3-(3,4-Methylenedioxyphenyl)-3-methyl-6-(6-phenoxypyridin-2-yl)-1-hexyne
3-(3,4-Methylenedioxyphenyl)-3-ethyl-6-(6-phenoxypyridin-2-yl)-1-hexene
3-(4-Allyloxyphenyl)-3-methyl-6-(6-phenoxypyridin-2-yl)-1-hexyne
3-(4-Allyloxyphenyl)-3-ethyl-6-(6-phenoxypyridin-2-yl)-1-hexene
3-(4-Allyloxyphenyl)-3-ethyl-6-(6-phenoxypyridin-2-yl)-1-hexyne
3-(4-Allyloxyphenyl)-6-(6-phenoxypyridin-2-yl)-1-hexene
3-(4-Allyloxyphenyl)-6-(6-phenoxypyridin-2-yl)-1-hexyne
3-(4-Chlorophenyl)-3-methyl-6-{3-(4-fluorophenoxy)-4-fluorophenyl}-1-hexene
3-(4-Chlorophenyl)-3-methyl-6-{3-(4-fluorophenoxy)-4-fluorophenyl}-1-hexyne
3-(4-Fluorophenyl)-3-methyl-6-{3-(4-fluorophenoxy)-4-fluorophenyl}-1-hexyne
3-(4-Fluorophenyl)-3-methyl-6-{3-(4-methylphenoxy)-4-fluorophenyl}-1-hexene
3-(4-Fluorophenyl)-3-methyl-6-{3-(4-methylphenoxy)-4-fluorophenyl}-1-hexyne
3-(4-Ethoxyphenyl)-3-methyl-6-{3-(4-fluorophenoxy)-4-fluorophenyl}-1-hexene
3-(4-Ethoxyphenyl)-3-methyl-6-{3-(4-fluorophenoxy)-4-fluorophenyl}-1-hexyne
3-(4-Ethoxyphenyl)-3-ethyl-6-{3-(4-fluorophenoxy)-4-fluorophenyl}-1-hexyne
3-(4-Ethoxyphenyl)-3-methyl-6-{3-(4-methylphenoxy)-4-fluorophenyl}-1-hexyne
3-(4-(Ethoxyphenyl)-3-methyl-6-{3-(4-methoxyphenoxy)phenyl}-1-hexyne
3-(4-(Ethoxyphenyl)-3-methyl-6-{3-(4-trifluoromethylphenoxy)phenyl}-1-hexyne
3-(4-Ethoxyphenyl)-6-{3-(4-fluorophenoxy)phenyl}-1-hexyne
3-(4-iso-Propyloxyphenyl)-3-methyl-6-{3-(4-fluorophenoxy)phenyl}-1-hexene
3-(4-iso-Propyloxyphenyl)-3-methyl-6-{3-(4fluorophenoxy)phenyl}-1-hexyne
3-(4-Ethoxyphenyl)-3-methyl-6-{3-(4-chlorophenoxy)phenyl}-1-hexene 3-(4-Ethoxyphenyl)-3-methyl-6-{3-(4-chlorophenoxy)phenyl}-1-hexyne
3-(4-iso-Propylphenyl)-3-methyl-6-{3-(4-fluorophenoxy)phenyl}-1-hexyne
3-(4-Trifluoromethylphenyl)-3-methyl-6-{3-(4-fluorophenoxy)phenyl}-1-hexyne
3-(4-Ethoxyphenyl)-3-ethyl-6-(6-phenoxypyridin-2-yl)-1-hexyne
3-(4-Ethoxyphenyl)-3-n-propyl-6-(6-phenoxypyridin-2-yl)-1-hexyne
3-(4-Ethoxyphenyl)-3-n-butyl-6-(6-phenoxypyridin-2-yl)-1-hexyne
3-(4-Ethoxyphenyl)-3-iso-propyl-6-(6-phenoxypyridin-2-yl)-1-hexyne
3-(4-iso-Propyloxyphenyl)-3-methyl-6-(6-phenoxypyridin-2-yl)-1-hexyne
3-(4-Allyloxyphyenyl)-3-methyl-6-(3-phenylthiophenyl)-1-hexyne
3-(3,4-Methylenedioxyphenyl)-3-methyl-6-(3-phenylthiophenyl)-1-hexyne
3-(4-Allyloxyphenyl)-3-methyl-6-(4-fluoro-3-phenylthiophenyl)-1-hexyne
3-(3,4-Methylenedioxyphenyl)-3-methyl-6-(4-fluoro-3-phenylthiophenyl)-1-hexyne
3-(4-Allyloxyphenyl)-3-methyl-6-{4-fluoro-3-(4-fluorophenylthio)phenyl}-1-hexyne
3-(3,4-Methylenedioxyphenyl)-3-methyl-6-{4-fluoro-3-(4-fluorophenylthio)phenyl}-1-hexyne
3-(4-Allyloxyphenyl)-3-methyl-6-{3-(4-chlorobenzyl)-4-fluorophenyl}-1-hexyne
3-(3,4-Methylenedioxyphenyl)-3-methyl-6-{3-(4-fluorobenzyl)-4-fluorophenyl}-1-hexyne
3-(4-Methoxyphenyl)-3-methyl-6-(3-phenylthiophenyl)-1-hexyne
3-(4-Ethoxyphenyl)-3-methyl-6-(3-phenylthiophenyl)-1-hexyne
3-(4-Ethoxyphenyl)-3-methyl-6-(4-fluoro-3-phenylthiophenyl)-1-hexene
3-(4-Ethoxyphenyl)-3-methyl-6-(4-fluoro-3-phenylthiophenyl)-1-hexyne
3-(4-Ethoxyphenyl)-3-methyl-6-{4-fluoro-3-(4-fluorophenylthio)phenyl}-1-hexyne
3-(4-Ethoxyphenyl)-3-methyl-6-{4-fluoro-3-(4-chlorophenylthio)phenyl}-1-hexyne
3-(4-Ethoxyphenyl)-3-methyl-6-{3-(4-chlorobenzyl)-4-fluorophenyl}-1-hexyne
3-(4-Ethoxyphenyl)-3-methyl 6-{3-(4-fluorobenzyl)-4-fluorophenyl}-1-hexyne
3-(3-Chloro-4-ethoxyphenyl)-3-n-propyl-6-(3-phenoxyphenyl)-1-hexene
3-(3-Chloro-4-ethoxyphenyl)-3-n-propyl-6-(3-phenoxyphenyl)-1-hexyne
3-(3-Chloro-4-ethoxyphenyl)-3-ethyl-6-(3-phenoxyphenyl)-1-hexyne
3-(3-Chloro-4-ethoxyphenyl)-3-methyl-6-(3-phenoxyphenyl)-1-hexene
3-(3-Chloro-4-ethoxyphenyl)-3-methyl-6-(3-phenoxyphenyl)-1-hexyne
3-(3-Chloro-4-ethoxyphenyl)-6-(3-phenoxyphenyl)-1-hexene
3-(3-Chloro-4-ethoxyphenyl)-6-(3-phenoxyphenyl)-1-hexyne
3-(3-Chloro-4-fluorophenyl)-3-methyl-6-(3-phenoxyphenyl)-1-hexene
3-(3-Chloro-4-fluorophenyl)-3-methyl-6-(3-phenoxyphenyl)-1-hexyne
3-(4-Allyloxyphenyl)-3-methyl-6-(3-phenoxyphenyl)-1-hexene
3-(4-Allyloxyphenyl)-3-methyl-6-(3-phenoxyphenyl)-1-hexyne
3-(4-Allyloxyphenyl)-3-ethyl-6-(3-phenoxyphenyl)-1-hexene
3-(4-Allyloxyphenyl)-3-ethyl-6-(3-phenoxyphenyl)-1-hexyne
3-(4-Allyloxyphenyl)-6-(3-phenoxyphenyl)-1-hexene
3-(4-Allyloxyphenyl)-6-(3-phenoxyphenyl)-1-hexyne
3-(4-Allyloxyphenyl)-3-iso-propyl-6-(3-phenoxyphenyl)-1-hexene
3-(4-Allyloxyphenyl)-3-iso-propyl-6-(3-phenoxyphenyl)-1-hexyne
3-(4-Allyloxyphenyl)-3-n-propyl-6-(3-phenoxyphenyl)-1-hexene
3-(4-iso-Propyloxyphenyl)-3-ethyl-6-(3-phenoxyphenyl)-1-hexene
3-(4-iso-Propyloxyphenyl)-3-ethyl-6-(3-phenoxyphenyl)-1-hexyne
3-(4-n-Propyloxyphenyl)-3-ethyl-6-(3-phenoxyphenyl)-1-hexene
3-(4-n-Propyloxyphenyl)-3-ethyl-6-(3-phenoxyphenyl)-1-hexyne
3-(4-iso-Propyloxyphenyl)-6-(3-phenoxyphenyl)-1-hexene
3-(4-iso-Propyloxyphenyl)-6-(3-phenoxyphenyl)-1-hexyne
3-(4-n-Propyloxyphenyl)-6-(3-phenoxyphenyl)-1-hexene
3-(4-n-Propyloxyphenyl)-6-(3-phenoxyphenyl)-1-hexyne
3-(4-n-Butyloxyphenyl)-3-ethyl-6-(3-phenoxyphenyl)-1-hexene
3-(4-Trifluoromethylphenyl)-3-methyl-6-(3-phenoxyphenyl)-1-hexene
3-(4-Trifluoromethylphenyl)-3-methyl-6-(3-phenoxyphenyl)-1-hexyne
3-(4-Trifluoromethylphenyl)-3-ethyl-6-(3-phenoxyphenyl)-1-hexene
3-(4-Trifluoromethylphenyl)-3-ethyl-6-(3-phenoxyphenyl)-1-hexyne
3-(4-Trifluoromethylphenyl)-6-(3-phenoxyphenyl)-1-hexene
3-(4-Trifluoromethylphenyl)-6-(3-phenoxyphenyl)-1-hexyne
3-(4-Trifluoromethylphenyl)-3-n-propyl-6-(3-phenoxyphenyl)-1-hexene
3-(4-Trifluoromethylphenyl)-3-n-propyl-6-(3-phenoxyphenyl)-1-hexyne
3-(4-Ethoxyphenyl)-3-methyl-6-{3-(4-methoxyphenoxy)-4-fluorophenyl}-1-hexyne
3-(4-Ethoxyphenyl)-3-methyl-6-{3-(4-trifluoromethylphenoxy)-4-fluorophenyl}-1-hexyne
3-(4-Ethoxyphenyl)-6-{3-(4-fluorophenoxy)-4-fluorophenyl}-1-hexyne
3-(4-iso-Propyloxyphenyl)-3-methyl-6-{3-(4-fluorophenoxy)-4-fluorophenyl}-1-hexene
3-(4-iso-Propyloxyphenyl)-3-methyl-6-{3-(4-fluorophenoxy)-4-fluorophenyl}-1-hexyne
3-(4-Ethoxyphenyl)-3-methyl-6-{3-(4-chlorophenoxy)-4-fluorophenyl}-1-hexene
3-(4-Ethoxyphenyl)-3-methyl-6-{3-(4-chlorophenoxy)-4-fluorophenyl}-1-hexyne
3-(4-iso-Propylphenyl)-3-methyl-6-{3-(4-fluorophenoxy)-4-fluorophenyl}-1-hexyne
3-(4-Trifluoromethylphenyl)-3-methyl-6-{3-(4-fluorophenoxy)-4-fluorophenyl}-1-hexyne
3-(4-Difluoromethoxyphenyl)-3-methyl-6-(3-anilino-4-fluorophenyl)-1-hexyne 3-(4-Difluoromethoxyphenyl)-3-ethyl-6-(3-anilino-4-fluorophenyl)-1-hexyne
3-(4-Difluoromethoxyphenyl)-6-(3-anilino-4-fluorophenyl)-1-hexene
3-(4-Difluoromethoxyphenyl)-6-(3-anilino-4-fluorophenyl)-1-hexyne
3-(3,4-Methylenedioxyphenyl)-3-methyl-6-(3-anilino-4-fluorophenyl)-1-hexene
3-(3,4-Methylenedioxyphenyl)-3-methyl-6-(3-anilino-4-fluorophenyl)-1-hexyne
3-(3,4-Methylenedioxyphenyl)-3-ethyl-6-(3-anilino-4-fluorophenyl)-1-hexyne
3-(3,4-Methylenedioxyphenyl)-3-n-propyl-6-(3-anilino-4-fluorophenyl)-1-hexyne
3-(3-Chloro-4-fluorophenyl)-3-methyl-6-(3-anilino-4-fluorophenyl)-1-hexyne
3-(4-Chlorophenyl)-3-methyl-6-(6-phenoxypyridin-2-yl)-1-hexene
3-(4-Chlorophenyl)-3-methyl-6-(6-phenoxypyridin-2-yl)-1-hexyne
3-(4-Chlorophenyl)-3-ethyl-6-(6-phenoxypyridin-2-yl)-1-hexene
3-(4-Chlorophenyl)-3-ethyl-6-(6-phenoxypyridin-2-yl)-1-hexyne
3-(4-Chlorophenyl)-3-n-propyl-6-(6-phenoxypyridin-2-yl)-1-hexene
3-(4-iso-Propyloxyphenyl)-3-ethyl-6-{3-(4-fluoroanilino)-4-fluorophenyl}-1-hexyne
3-(4-Allyloxyphenyl)-3-methyl-6-{3-(4-chloroanilino)-4-fluorophenyl}-1-hexene
3-(4-Allyloxyphenyl)-3-methyl-6-{3-(4-fluoroanilino)-4-fluorophenyl}-1-hexene
3-(4-Allyloxyphenyl)-3-methyl-6-{3-(4-chloroanilino)-4-fluorophenyl}-1-hexyne
3-(4-Allyloxyphenyl)-3-methyl-6-{3-(4-fluoroanilino)-4-fluorophenyl}-1-hexyne
3-(4-Allyloxyphenyl)-3-ethyl-6-{3-(4-methylanilino)-4-fluorophenyl}-1-hexyne
3-(4-Difluoromethoxyphenyl)-3-methyl-6-{3-(4-fluoroanilino)-4-fluorophenyl}-1-hexyne
3-(4-Difluoromethoxyphenyl)-6-{3-(4-fluoroanilino)-4-fluorophenyl}-1-hexene
3-(4-Difluoromethoxyphenyl)-3-ethyl-6-{3-(4-chloroanilino)-4-fluorophenyl}-1-hexyne
3-(4-Ethylphenyl)-3-methyl-6-(3-anilino-4-fluorophenyl)-1-hexyne
3-(4-iso-Propylphenyl)-3-methyl-6-(3-anilino-4-fluorophenyl)-1-hexyne
3-(4-Trifluoromethylphenyl)-3-methyl-6-(3-anilino-4-fluorophenyl)-1-hexene
3-(4-Trifluoromethylphenyl)-3-methyl-6-(3-anilino-4-fluorophenyl)-1-hexyne
3-(4-Trifluoromethylphenyl)-3-ethyl-6-(3-anilino-4-fluorophenyl)-1-hexyne
3-(4-Methoxyphenyl)-3-methyl-6-(3-anilino-4-fluorophenyl)-1-hexyne
3-(4-Methoxyphenyl)-3-ethyl-6-(3-anilino-4-fluorophenyl)-1-hexyne
3-(4-Ethoxyphenyl)-3-methyl-6-(3-anilino-4-fluorophenyl)-1-hexyne
3-(4-Ethoxyphenyl)-3-methyl-6-(3-anilino-4-fluorophenyl)-1-hexene
3-(3-Chloro-4-ethoxyphenyl)-3-methyl-6-{3-(4-fluoroanilino)-4-fluorophenyl}-1-hexyne
3-(3-Chloro-4-ethoxyphenyl)-6-{3-(4-fluoroanilino)-4-fluorophenyl}-1-hexyne
3-(3-Chloro-4-ethoxyphenyl)-6-{3-(4-fluoroanilino)-4-fluorophenyl}-1-hexene
3-(3-Chloro-4-ethoxyphenyl)-3-methyl-6-{3-(4-trifluoromethylanilino)-4-fluorophenyl}-1-hexyne
3-(4-Chlorophenyl)-3-methyl-6-(3-anilino-4-fluorophenyl)-1-hexene
3-(4-Chlorophenyl)-3-methyl-6-(3-anilino-4-fluorophenyl)-1-hexyne
3-(4-Chlorophenyl)-3-ethyl-6-(3-anilino-4-fluorophenyl)-1-hexene
3-(4-Chlorophenyl)-3-ethyl-6-(3-anilino-4-fluorophenyl)-1-hexyne
3-(4-Chlorophenyl)-6-(3-anilino-4-fluorophenyl)-1-hexyne
3-(4-Chlorophenyl)-6-(3-anilino-4-fluorophenyl)-1-hexene
3-(4-Fluorophenyl)-3-methyl-6-(3-anilino-4-fluorophenyl)-1-hexene
3-(4-Fluorophenyl)-3-methyl-6-(3-anilino-4-fluorophenyl)-1-hexyne
3-(4-Fluorophenyl)-3-ethyl-6-(3-anilino-4-fluorophenyl)-1-hexyne
3-(4-Difluoromethoxyphenyl)-3-n-propyl-6-{3-(4-fluoroanilino)-4-fluorophenyl}-1-hexyne
3-(3,4-Methylenedioxyphenyl)-3-methyl-6-{3-(4-chloroanilino)-4-fluorophenyl}-1-hexyne
3-(3,4-Methylenedioxyphenyl)-3-methyl-6-{3-(4-trifluoromethylanilino)-4-fluorophenyl}-1-hexyne
3-(3,4-Methylenedioxyphenyl)-3-ethyl-6-{3-(4-fluoroanilino)-4-fluorophenyl}-1-hexyne
3-(3,4-Dichlorophenyl)-3-methyl-6-{3-(4-chloroanilino)-4-fluorophenyl}-1-hexyne
3-(3,4-Dichlorophenyl)-3-methyl-6-{3-(4-fluoroanilino)-4-fluorophenyl}-1-hexyne
3-(3-Chloro-4-fluorophenyl)-3-methyl-6-{3-(4-methylanilino)-4-fluorophenyl}-1-hexyne
3-(3-Chloro-4-fluorophenyl)-3-methyl-6-{3-(4-fluoroanilino)-4-fluorophenyl}-1-hexyne
3-(3-Chloro-4-methylphenyl)-3-methyl-6-{3-(4-fluoroanilino)-4-fluorophenyl}-1-hexyne
3-(4-tert-Butylphenyl)-3-methyl-6-{3-(4-fluoroanilino)-4-fluorophenyl}-1-hexyne
3-(4-Ethylphenyl)-3-methyl-6-{3-(4-chloroanilino)-4-fluorophenyl}-1-hexyne
3-(4-Trifluoromethylphenyl)-3-methyl-6-{3-(4-fluoroanilino)-4-fluorophenyl}-1-hexyne
3-(4-Trifluoromethylphenyl)-3-methyl-6-{3-(4-fluoroanilino)-4-fluorophenyl}-1-hexene
3-(4-Trifluoromethylphenyl)-3-ethyl-6-{3-(4-chloroanilino)-4-fluorophenyl}-1-hexyne
3-(4-Trifluoromethylphenyl)-6-{3-(4-fluoroanilino)-4-fluorophenyl}-1-hexyne
3-(4-Methoxyphenyl)-3-methyl-6-{3-(4-fluoroanilino)-4-fluorophenyl}-1-hexyne
3-(4-Methoxyphenyl)-3-methyl-6-{3-(4-chloroanilino)-4-fluorophenyl}-1-hexyne
3-(4-Methoxyphenyl)-3-methyl-6-{3-(4-methylanilino)-4-fluorophenyl}-1-hexyne
3-(4-Methylphenyl)-3-methyl-6-(3-phenoxy-4-fluorophenyl)-1-hexene
3-(4-Methylphenyl)-3-methyl-6-(3-phenoxy-4-fluorophenyl)-1-hexyne
3-(4-Ethylphenyl)-3-methyl-6-(3-phenoxy-4-fluorophenyl)-1-hexyne
3-(4-n-Propylphenyl)-3-methyl-6-(3-phenoxy-4-fluorophenyl)-1-hexyne
3-(4-tert-Butylphenyl)-3-methyl-6-(3-phenoxy-4-fluorophenyl)-1-hexyne
3-(4-n-Butylphenyl)-3-methyl-6-(3-phenoxy-4-fluorophenyl)-1-hexyne 3-(4-iso-Propylphenyl)-3-methyl-6-(3-phenoxy-4-fluorophenyl)-1-hexyne
3-(4-Methylphenyl)-3-ethyl-6-(3-phenoxy-4-fluorophenyl)-1-hexene
3-(4-Methylphenyl)-3-ethyl-6-(3-phenoxy-4-fluorophenyl)-1-hexyne
3-(4-Chlorophenyl)-3-n-propyl-6-(6-phenoxypyridin-2-yl)-1-hexyne
3-(4-Fluorophenyl)-3-methyl-6-(6-phenoxypyridin-2-yl)-1-hexene
3-(4-Fluorophenyl)-3-methyl-6-(6-phenoxypyridin-2-yl)-1-hexyne
3-(4-Fluorophenyl)-3-ethyl-6-(6-phenoxypyridin-2-yl)-1-hexyne
3-(4-iso-Propylphenyl)-3-methyl-6-(6-phenoxypyridin-2-yl)-1-hexyne
3-(4-Ethoxyphenyl)-3-methyl-6-(4-fluoro-6-phenoxypyridin-2-yl)-1-hexene
3-(4-Ethoxyphenyl)-3-ethyl-6-(4-fluoro-6-phenoxypyridin-2-yl)-1-hexyne
3-(4-Ethoxyphenyl)-3-ethyl-6-(4-fluoro-6-phenoxypyridin-2-yl)-1-hexyne
3-(4-Ethoxyphenyl)-3-n-propyl-6-(4-fluoro-6-phenoxypyridin-2-yl)-1-hexyne
3-(4-Ethoxyphenyl)-3-methyl-6-(6-phenoxypyridin-2-yl)-1-hexene
3-(4-Ethoxyphenyl)-3-methyl-6-(6-phenoxypyridin-2-yl)-1-hexyne
3-(4-Ethoxyphenyl)-6-(6-phenoxypyridin-2-yl)-1-hexene
3-(4-Ethoxyphenyl)-6-(6-phenoxypyridin-2-yl)-1-hexyne
3-(4-Ethoxyphenyl)-3-ethyl-6-(6-phenoxypyridin-2-yl)-1-hexene
3-(3,4-Methylenedioxyphenyl)-3-methyl-6-(4-fluoro-6-phenoxypyridin-2-yl)-1-hexyne
3-(3-Chloro-4-fluorophenyl)-3-methyl-6-(4-fluoro-6-phenoxypyridin-2-yl)-1-hexyne
3-(3-Chloro-4-ethoxyphenyl)-3-methyl-6-(4-fluoro-6-phenoxypyridin-2-yl)-1-hexyne
3-(3,4-Dichlorophenyl)-3-methyl-6-(4-fluoro-6-phenoxypyridin-2-yl)-1-hexyne
3-(4-Ethoxyphenyl)-3-methyl-6-{3-(4-fluoroanilino)-4-fluorophenyl}-1-hexyne
3-(4-Ethoxyphenyl)-3-methyl-6-{3-(4-fluoroanilino)-4-fluorophenyl}-1-hexene
3-(4-Ethoxyphenyl)-3-methyl-6-{3-(4-chloroanilino)-4-fluorophenyl}-1-hexene
3-(4-Ethoxyphenyl)-3-methyl-6-{3-(4-chloroanilino)-4-fluorophenyl}-1-hexyne
3-(4-Ethoxyphenyl)-3-methyl-6-{3-(4-methylanilino)-4-fluorophenyl}-1-hexene
3-(4-Ethoxyphenyl)-3-methyl-6-{3-(4-methylanilino)-4-fluorophenyl}-1-hexyne
3-(4-Ethoxyphenyl)-3-methyl-6-{3-(4-trifluoromethylanilino)-4-fluorophenyl}-1-hexyne
3-(4-Ethoxyphenyl)-3-ethyl-6-{3-(4-fluoroanilino)-4-fluorophenyl}-1-hexene
3-(4-Ethoxyphenyl)-3-ethyl-6-{3-(4-fluoroanilino)-4-fluorophenyl}-1-hexyne
3-(4-Chlorophenyl)-3-methyl-6-(3-phenoxy-4-fluorophenyl)-1-hexene
3-(4-Chlorophenyl)-3-methyl-6-(3-phenoxy-4-fluorophenyl)-1-hexyne
3-(4-Chlorophenyl)-3-ethyl-6-(3-phenoxy-4-fluorophenyl)-1-hexene
3-(4-Chlorophenyl)-3-ethyl-6-(3-phenoxy-4-fluorophenyl)-1-hexyne
3-(4-Fluorophenyl)-3-methyl-6-(3-phenoxy-4-fluorophenyl)-1-hexene
3-(4-Fluorophenyl)-3-methyl-6-(3-phenoxy-4-fluorophenyl)-1-hexyne
3-(4-Fluorophenyl)-3-ethyl-6-(3-phenoxy-4-fluorophenyl)-1-hexene
3-(4-Fluorophenyl)-3-ethyl-6-(3-phenoxy-4-fluorophenyl)-1-hexyne
3-(4-Chlorophenyl)-3-n-propyl-6-(3-phenoxy-4-fluorophenyl)-1-hexyne
3-(4-Ethoxyphenyl)-3-n-butyl-6-(3-phenoxy-4-fluorophenyl)-1-hexyne
3-(4-Ethoxyphenyl)-3-n-propyl-6-(3-phenoxy-4-fluorophenyl)-1-hexene
3-(4-Ethoxyphenyl)-3-n-propyl-6-(3-phenoxy-4-fluorophenyl)-1-hexyne
3-(4-Ethoxyphenyl)-3-iso-propyl-6-(3-phenoxy-4-fluorophenyl)-1-hexene
3-(4-Ethoxyphenyl)-3-iso-propyl-6-(3-phenoxy-4-fluorophenyl)-1-hexyne
3-(4-n-Propyloxyphenyl)-3-methyl-6-(3-phenoxy-4-fluorophenyl)-1-hexene
3-(4-n-Propyloxyphenyl)-3-methyl-6-(3-phenoxy-4-fluorophenyl)-1-hexyne
3-(4-iso-Propyloxyphenyl)-3-methyl-6-(3-phenoxy-4-fluorophenyl)-1-hexene
3-(4 iso-Propyloxyphenyl)-3-methyl-6-(3-phenoxy-4-fluorophenyl)-1-hexyne
3-(4-Chlorophenyl)-3-methyl-6-{3-(4-fluoroanilino)-4-fluorophenyl}-1-hexene
3-(4-Chlorophenyl)-3-methyl-6-{3-(4-fluoroanilino)-4-fluorophenyl}-1-hexyne
3-(4-Fluorophenyl)-3-methyl-6-{3-(4-fluoroanilino)-4-fluorophenyl}-1-hexyne
3-(4-Fluorophenyl)-3-methyl-6-{3-(4-chloroanilino)-4-fluorophenyl}-1-hexyne
3-(4-Fluorophenyl)-3-ethyl-6-{3-(4-fluoroanlino)-4-fluorophenyl}-1-hexyne
3-(4-iso-Propylphenyl)-3-methyl-6-{3-(4-methylanilino)-4-fluorophenyl}-1-hexene
3-(4-iso-Propylphenyl)-3-methyl-6-{3-(4-fluoroanilino)-4-fluorophenyl}-1-hexyne
3-(4-iso-Propylphenyl)-3-methyl-6-{3-(4-chloroanilino)-4-fluorophenyl}-1-hexyne
3-(4-iso-Propylphenyl)-3-methyl-6-{3-(4-trifluoromethylanilino)-4-fluorophenyl}-1-hexyne
3-(3,4-Difluorophenyl)-3-ethyl-6-(3-phenoxyphenyl)-1-hexyne
3-(3,4-Difluorophenyl)-3-methyl-6-(3-phenoxyphenyl)-1-hexyne
3-(3,4-Difluorophenyl)-3-methyl-6-(3-phenoxyphenyl)-1-hexene
3-(3,4-Diethoxyphenyl)-3-methyl-6-(3-phenoxyphenyl)-1-hexene
3-(3,4-Diethoxyphenyl)-3-methyl-6-(3-phenoxyphenyl)-1-hexyne
3-(4-iso-Propyloxyphenyl)-3-ethyl-6-(3-phenoxy-4-fluorophenyl)-1-hexene
3-(4-iso-Propyloxyphenyl)-3-ethyl-6-(3-phenoxy-4-fluorophenyl)-1-hexyne
3-(4-n-Propyloxyphenyl)-3-ethyl-6-(3-phenoxy-4-fluorophenyl)-1-hexene
3-(4-n-Propyloxyphenyl)-3-ethyl-6-(3-phenoxy-4-fluorophenyl)-1-hexyne
3-(4-iso-Propyloxyphenyl)-6-(3-phenoxy-4-fluorophenyl)-1-hexene
3-(4-iso-Propyloxyphenyl)-6-(3-phenoxy-4-fluorophenyl)-1-hexyne 3-(4-n-Propyloxyphenyl)-6-(3-phenoxy-4-fluorophenyl)-1-hexene
3-(4-n-Propyloxyphenyl)-6-(3-phenoxy-4-fluorophenyl)-1-hexyne
3-(4-n-Butyloxyphenyl)-3-ethyl-6-(3-phenoxy-4-fluorophenyl)-1-hexene
3-(4-Ethoxyphenyl)-3-n-propyl-6-{3-(4-fluoroanilino)-4-fluorophenyl}-1-hexyne
3-(4-Ethoxyphenyl)-3-n-propyl-6-{3-(4-chloroanilino)-4-fluorophenyl}-1-hexyne
3-(4-Ethoxyphenyl)-6-{3-(4-fluoroanilino)-4-fluorophenyl}1-hexyne
3-(4-Ethoxyphenyl)-6-{3-(4-fluoroanilino)-4-fluorophenyl}1-hexene
3-(4-Ethoxyphenyl)-3-methyl-6-{3-(tertbutylanilino)-4-fluorophenyl}-1-hexyne
3-(4-Ethoxyphenyl)-3-iso-propyl-6-{3-(4-fluoroanilino)-4-fluorphenyl}-1-hexyne
3-(4-Ethoxyphenyl)-3-n-propyl-6-{3-(4-fluoroanilino)-4-fluorophenyl}-1-hexyne
3-(4-n-Propyloxyphenyl)-3-methyl-6-{3-(4-fluoroanilino)-4-fluorophenyl}-1-hexyne
3-(4-n-Propyloxyphenyl)-3-methyl-6-{3-(4-chloroanilino)-4-fluorophenyl)-}1-hexyne
3-(4-iso-Propyloxyphenyl)-3-methyl-6-{3-(4-methylanlino)-4-fluorophenyl}-1-hexyne
3-(4-Allyloxyphenyl)-3-methyl-6-(3-phenoxy-4-fluorophenyl)-1-hexyne
3-(4-Allyloxyphenyl)-3-methyl-6-(3-phenoxy-4-fluorophenyl)-1-hexene
3-(4-Allyloxyphenyl)-3-ethyl-6-(3-phenoxy-4-fluorophenyl)-1-hexyne
3-(4-Allyloxyphenyl)-3-ethyl-6-(3-phenoxy-4-fluorophenyl)-1-hexene
3-(4-Allyloxyphenyl)-6-(3-phenoxy-4-fluorophenyl-1-hexyne
3-(4-Allyloxyphenyl)-3-iso-propyl-6-(3-phenoxy-4-fluorophenyl)-1-hexene
3-(4-Allyloxyphenyl)-3-iso-propyl-6-(3-phenoxy-4-fluorophenyl)-1-hexyne
3-(4-Allyloxyphenyl)-3-n-propyl-6-(3-phenoxy-4-fluorophenyl)-1-hexene
3-(4-Allyloxyphenyl)-3-n-propyl-6-(3-phenoxy-4-fluorophenyl)-1-hexyne
3-(4-Difluoromethoxyphenyl)-3-methyl-6-(3-phenoxy-4-fluorophenyl)-1-hexene
3-(4-Difluoromethoxyphenyl)-3-methyl-6-(3-phenoxy-4-fluorophenyl)-1-hexyne
3-(4-Difluoromethoxyphenyl)-3-ethyl-6-(3-phenoxy-4-fluorophenyl)-1-hexene
3-(4-Difluoromethoxyphenyl)-3-ethyl-6-(3-phenoxy-4-fluorophenyl)-1-hexyne
3-(4-Difluoromethoxyphenyl)-6-(3-phenoxy-4-fluorophenyl)-1-hexene
3-(4-Difluoromethoxyphenyl)-6-(3-phenoxy-4-fluorophenyl)-1-hexyne
3-(4-Difluoromethoxyphenyl)-3-n-propyl-6-(3-phenoxy-4-fluorophenyl)-1-hexene
3-(4-Difluoromethoxyphenyl)-3-n-propyl-6-(3-phenoxy-4-fluorophenyl)-1-hexyne
3-(3,4-Difluorophenyl)-3-ethyl-6-(3-phenoxy-4-fluorophenyl)-1-hexyne
3-(3,4-Difluorophenyl)-3-methyl-6-(3-phenoxy-4-fluorophenyl)-1-hexyne
3-(3,4-Difluorophenyl)-3-methyl-6-(3-phenoxy-4-fluorophenyl)-1-hexene
3-(3,4-Diethoxyphenyl)-3-methyl-6-(3-phenoxy-4-fluorophenyl)-1-hexene
3-(3,4-Diethoxyphenyl)-3-methyl-6-(3-phenoxy-4-fluorophenyl)-1-hexyne
3-(4-Fluorophenyl)-3-methyl-6-(3-benzylphenyl)-1-hexene
3-(4-Methoxyphenyl)-3-methyl-6-(3-benzylphenyl)-1-hexyne
3-(4-Ethoxyphenyl)-3-methyl-6-(3-benzylphenyl)-1-hexene
3-(4-Ethoxyphenyl)-3-methyl-6-(3-benzylphenyl)-1-hexyne
3-(4-Methoxyphenyl)-3-ethyl-6-(3-benzyl-4-fluorophenyl)-1-hexyne
3-(4-Ethoxyphenyl)-3-methyl-6-(3-benzyl-4-fluorophenyl)-1-hexyne
3-(4-Ethoxyphenyl)-3-methyl-6-(3-benzyl-4-fluorophenyl)-1-hexene
3-(4-Ethoxyphenyl)-3-ethyl-6-(3-benzyl-4-fluorophenyl)-1-hexyne
3-(4-Trifluoromethylphenyl)-3-methyl-6-(3-phenoxy-4-fluorophenyl)-1-hexene
3-(4-Trifluoromethylphenyl)-3-methyl-6-(3-phenoxy-4-fluorophenyl)-1-hexyne
3-(4-Trifluoromethylphenyl)-3-ethyl-6-(3-phenoxy-4-fluorophenyl)-1-hexene
3-(4-Trifluoromethylphenyl)-3-ethyl-6-(3-phenoxy-4-fluorophenyl)-1-hexyne
3-(4-Trifluoromethylphenyl)-6-(3-phenoxy-4-fluorophenyl)-1-hexene
3-(4-Trifluoromethylphenyl)-6-(3-phenoxy-4-fluorophenyl)-1-hexyne
3-(4-Trifluoromethylphenyl)-3-n-propyl-6-(3-phenoxy-4-fluorophenyl)-1-hexene
3-(4-Trifluoromethylphenyl)-3-n-propyl-6-(3-phenoxy-4-fluorophenyl)-1-hexyne
3-(4-n-Propylphenyl)-3-methyl-6-(6-phenoxypyridin-2-yl)-1-hexene
3-(4-n-Propylphenyl)-3-methyl-6-(6-phenoxypyridin-2-yl)-1-hexyne
3-(4-Trifluoromethylphenyl)-3-methyl-6-(6-phenoxypyridin-2-yl)-1-hexene
3-(4-Trifluoromethylphenyl)-3-methyl-6-(6-phenoxypyridin-2-yl)-1-hexyne
3-(4-Trifluoromethylphenyl)-3-ethyl-6-(6-phenoxypyridin-2-yl)-1-hexene
3-(4-Ethoxyphenyl)-6-(4-fluoro-6-phenoxypyridin-2-yl)-1-hexyne
3-(4-iso-Propyloxyphenyl)-3-methyl-6-(4-fluoro-6-phenoxypyridin-2-yl)-1-hexyne
3-(4-iso-Propylphenyl)-3-methyl-6-(4-fluoro-6-phenoxypyridin-2-yl)-1-hexyne
3-(4-Trifluoromethylphenyl)-3-methyl-6-(4-fluoro-6-phenoxypyridin-2-yl)-1-hexyne
3-(3,4-Methylenedioxyphenyl)-3-n-propyl-6-(3-phenoxy-4-fluorophenyl)-1-hexene
3-(3,4-Methylenedioxyphenyl)-3-n-propyl-6-(3-phenoxy-4-fluorophenyl)-1-hexyne
3-(3,4-Methylenedioxyphenyl)-3-methyl-6-(3-phenoxy-4-fluorophenyl)-1-hexene
3-(3,4-Methylenedioxyphenyl)-3-methyl-6-(3-phenoxy-4-fluorophenyl)-1-hexyne
3-(3,4-Methylenedioxyphenyl)-3-ethyl-6-(3-phenoxy-4-fluorophenyl)-1-hexene
3-(3,4-Methylenedioxyphenyl)-3-ethyl-6-(3-phenoxy-4-fluorophenyl)-1-hexyne
3-(3,4-Methylenedioxyphenyl)-6-(3-phenoxy-4-fluorophenyl)-1-hexene
3-(3,4-Methylenedioxyphenyl)-6-(3-phenoxy-4-fluorophenyl)-1-hexyne 3-(4-Trifluoromethylphenyl)-3-ethyl-6-(6-phenoxypyrdin-2-yl)-1-hexyne 3-(4-Trifluoromethylphenyl)-6-(6-phenoxypyridin-2-yl)-1-hexene 3-(4-Trifluoromethylphenyl)-6-(6-phenoxypyridin-2-yl)-1-hexyne 3-(4-Trifluoromethylphenyl)-3-n-propyl-6-(6-phenoxypyridin-2-yl)-1-hexyne 3-(4-Methoxyphenyl)-3-methyl-6-(6-phenoxypyridin-2-yl)-1-hexyne 3-(4-Allyloxyphenyl)-3-methyl-6-(4-fluoro-6-phenoxypyrdin-2-yl)-1-hexyne 3-(4-Allyloxyphenyl)-3-methyl-6-(4-fluoro-6-phenoxypyrdin-2-yl)-1-hexene 3-(4-Difluoromethoxyphenyl)-3-methyl-6-(4-fluoro-6-phenoxypyridin-2-yl)-1-hexyne 3-(4-Difluoromethoxyphenyl)-3-ethyl-6-(4-fluoro-6-phenoxypyridin-2-yl)-1-hexyne 3-(3-Chloro-4-fluorophenyl)-3-ethyl-6-(3-phenoxy-4-fluorophenyl)-1-hexyne 3-(3-Chloro-4-fluorophenyl)-6-(3-phenoxy-4-fluorophenyl)-1-hexyne 3-(3,4-Dichlorophenyl)-3-methyl-6-(3-phenoxy-4-fluorophenyl)-1-hexyne 3-(3,4-Dichlorophenyl)-3-methyl-6-(3-phenoxy-4-fluorophenyl)-1-hexene 3-(3,4-Dichlorophenyl)-3-ethyl-6-(3-phenoxy-4-fluorophenyl)-1-hexyne 3-(3-Chloro-4-methylphenyl)-3-methyl-6-(3-phenoxy-4-fluorophenyl)-1-hexyne 3-(3,4-Dimethylphenyl)-3-methyl-6-(3-phenoxy-4-fluorophenyl)-1-hexyne 3-(3-Fluoro-4-chlorophenyl)-3-methyl-6-(3-phenoxy-4-fluorophenyl)-1-hexyne 3-(3-Fluoro-4-chlorophenyl)-3-methyl-6-(3-phenoxy-4-fluorophenyl)-1-hexene 3-(4-Ethoxyphenyl)-3-ethyl-6-(3-anilino-4-fluorophenyl)-1-hexene 3-(4-Ethoxyphenyl)-3-ethyl-6-(3-anilino-4-fluorophenyl)-1-hexyne 3-(4-Ethoxyphenyl)-3-n-propyl-6-(3-anilino-4-fluorophenyl)-1-hexene 3-(4-Ethoxyphenyl)-3-n-propyl-6-(3-anilino-4-fluorophenyl)-1-hexyne 3-(4-Ethoxyphenyl)-6-(3-anilino-4-fluorophenyl)-1-hexene 3-(4-Ethoxyphenyl)-6-(3-anilino-4-fluorophenyl)-1-hexyne 3-(4-iso-Propyloxyphenyl)-3-methyl-6-(3-anilino-4-fluorophenyl)-1-hexene 3-(4-iso-Propyloxyphenyl)-3-methyl-6-(3-anilino-4-fluorophenyl)-1-hexyne 3-(4-n-Propyloxyphenyl)-3-methyl-6-(3-anilino-4-fluorophenyl)-1-hexene 3-(4-Chlorophenyl)-3-methyl-6-(3-benzylphenyl)-1-hexyne 3-(4-Fluorophenyl)-3-methyl-6-(3-benzylphenyl)-1-hexyne 3-(4-iso-Propylphenyl)-3-methyl-6-(3-benzylphenyl)-1-hexyne 3-(4-Fluorophenyl)-3-ethyl-6-(3-benzylphenyl)1-hexyne 3-(4-Chlorophenyl)-3-methyl-6-(3-benzyl-4-fluoro-phenyl)-1-hexyne 3-(4-Fluorophenyl)-3-methyl-6-(3-benzyl-4-fluorophenyl)-1-hexyne 3-(4-n-Propylphenyl)-3-methyl-6-(3-benzyl-4-fluorophenyl)-1-hexyne 3-(4-Methoxyphenyl)-3-methyl-6-(3-benzyl-4-fluorophenyl)-1-hexyne 3-(4-Methoxyphenyl)-3-methyl-6-(3-phenoxy-4-fluorophenyl)-1-hexene 3-(4-Methoxyphenyl)-3-methyl-6-(3-phenoxy-4-fluorophenyl)-1-hexyne 3-(4-Ethoxyphenyl)-3-methyl-6-(3-phenoxy-4-fluorophenyl)-1-hexene 3-(4-Ethoxyphenyl)-3-methyl-6-(3-phenoxy-4-fluorophenyl)-1-hexyne 3-(4-Ethoxyphenyl)-3-ethyl-6-(3-phenoxy-4-fluorophenyl)-1-hexene 3-(4-Ethoxyphenyl)-3-ethyl-6-(3-phenoxy-4-fluorophenyl)-1-hexyne 3-(4-Ethoxyphenyl)-6-(3-phenoxy-4-fluorophenyl)1-hexene 3-(4-Ethoxyphenyl)-6-(3-phenoxy-4-fluorophenyl)-1-hexyne 3-(4-Ethoxyphenyl)-3-n-butyl-6-(3-phenoxy-4-fluorophenyl)-1-hexene 3-(3-Chloro-4-ethoxyphenyl)-3-n-propyl-6-(3-phenoxy-4-fluorophenyl)-1-hexene 3-(3-Chloro-4-ethoxyphenyl)-3-n-propyl-6-(3-phenoxy-4-fluorophenyl)-1-hexyne 3-(3-Chloro-4-ethoxyphenyl)-3-ethyl-6-(3-phenoxy-4-fluorophenyl)-1-hexyne 3-(3-Chloro-4-ethoxyphenyl)-3-methyl-6-(3-phenoxy-4-fluorophenyl)-1-hexene 3-(3-Chloro-4-ethoxyphenyl)-3-methyl-6-(3-phenoxy-4-fluorophenyl)-1-hexyne 3-(3-Chloro-4-ethoxyphenyl)-6-(3-phenoxoy-4-fluorophenyl)-1-hexene 3-(3-Chloro-4-ethoxyphenyl)-6-(3-phenoxoy-4-fluorophenyl)-1-hexyne 3-(3-Chloro-4-fluorophenyl)-3-methyl-6-(3-phenoxy-4-fluorophenyl)-1-hexene 3-(3-Chloro-4-fluorophenyl)-3-methyl-6-(3-phenoxy-4-fluorophenyl)-1-hexyne 3-(3-Chloro-4-fluorophenyl)-3-ethyl-6-(3-phenoxyphenyl)-1-hexyne 3-(3-Chloro-4-fluorophenyl)-6-(3-phenoxyphenyl)-1-hexyne 3-(3,4-Dichlorophenyl)-3-methyl-6-(3-phenoxyphenyl)-1-hexyne 3-(3,4-Dichlorophenyl)-3-methyl-6-(3-phenoxyphenyl)-1-hexene 3-(3,4-Dichlorophenyl)-3-ethyl-6-(3-phenoxyphenyl)-1-hexyne 3-(Chloro-4-methylphenyl)-3-methyl-6-(3-phenoxyphenyl)-1-hexyne 3-(3,4-Dimethylphenyl)-3-methyl-6-(3-phenoxyphenyl)-1-hexyne 3-(3-Fluoro-4-chlorophenyl)-3-methyl-6-(3-phenoxyphenyl)-1-hexyne 3-(3-Fluoro-4-chlorophenyl)-3-methyl-6-(3-phenoxyphenyl)-1-hexene 3-(4-n-Butyloxyphenyl)-3-ethyl-6-(3-phenoxy-4-fluorophenyl)-1-hexyne 3-(4-n-Butyloxyphenyl)-3-methyl-6-(3-phenoxy-4-fluorophenyl)-1-hexene 3-(4-n-Butyloxyphenyl)-3-methyl-6-(3-phenoxy-4-fluorophenyl)-1-hexyne 3-(4-n-Butyloxyphenyl)-6-(3-phenoxy-4-fluorophenyl)-1-hexene 3-(4-n-Butyloxyphenyl) -6-(3-phenoxy-4-fluorophenyl)-1-hexyne 3-(4-iso-Butyloxyphenyl)-3-methyl-6-(3-phenoxy-4-fluorophenyl)-1-hexene 3-(4-iso-Butyloxyphenyl)-3-methyl-6-(3-phenoxy-4-fluorophenyl)-1-hexyne
3-(4-Trifluoromethylphenyl)-3-methyl-6-(3-benzylphenyl)-1-hexene
3-(4-Trifluoromethylphenyl)-3-methyl-6-(3-benzylphenyl)-1-hexyne
3-(4-Allyloxyphenyl)-3-methyl-6-(3-benzylphenyl)-1-hexyne
3-(4-Difluoromethoxyphenyl)-3-methyl-6-(3-benzylphenyl)-1-hexyne
3-(3-Chloro-4-ethoxyphenyl)-3-methyl-6-(3-benzyl-4-fluorophenyl)-1-hexyne
3-(4-Ethoxyphenyl)-6-(3-benzyl-4-fluorophenyl)-1-hexene
3-(4-Ethoxyphenyl)-6-(3-benzyl-4-fluorophenyl-1-hexyne
3-(3-Fluorophenyl)-3-methyl-6-(3-phenoxy-4-fluorophenyl)-1-hexyne
3-(3-Ethoxyphenyl)-3-methyl-6-(3-phenoxy-4-fluorophenyl)-1-hexyne
3-(4-Trifluoromethoxyphenyl)-3-methyl-6-(3-phenoxyphenyl)-1-hexyne
3-(4-Trifluoromethoxyphenyl)-3-methyl-6-(3-phenoxy-4-fluorophenyl)-1-hexyne
3-(4-Trifluoromethoxyphenyl)-3-methyl-6-(3-anilino-4-fluorophenyl)-1-hexyne
3-(4-Trifluoromethoxyphenyl)-3-ethyl-6-(3-phenoxy-4-fluorophenyl)-1-hexyne
3-(3-Trifluoromethoxyphenyl)-3-methyl-6-(3-phenoxy-4-fluorophenyl)-1-hexyne Examples of the compounds thus obtained are shown in Table 1, but the present compounds are not limited to these examples.

TABLE 1

(I)

*Structural formula:* aromatic rings with substituents $R_1, R_2, R_3, R_4, R_5, R_6$, $Y$ and $Z$ per the general formula (I)

| Compound No. | R₁ | R₂ | R₃ | R₄ | R₅ | R₆ | Y | Z | Physical property [refractive index nD(°C.)] |
|---|---|---|---|---|---|---|---|---|---|
| (1) | —OC₂H₅ | H | —CH=CH₂ | —CH₃ | H | H | O | CH | 1.5740 (24.5) |
| (2) | —OC₂H₅ | H | —CH=CH₂ | —CH₃ | F | H | O | CH | 1.5638 (24.0) |
| (3) | —OC₂H₅ | H | —C≡CH | —CH₃ | H | H | O | CH | 1.5721 (18.5) |
| (4) | —OC₂H₅ | H | —C≡CH | —CH₃ | F | H | O | CH | 1.5615 (20.5) |
| (5) | —OCH₃ | H | —C≡CH | —CH₃ | F | H | O | CH | 1.5642 (25.5) |
| (6) | —OCHF₂ | H | —C≡CH | —CH₃ | F | H | O | CH | 1.5436 (25.0) |
| (7) | —OCH₂CH=CH₂ | H | —C≡CH | —CH₃ | H | H | O | CH | 1.5821 (20.0) |
| (8) | —OCH₂CH=CH₂ | H | —C≡CH | —CH₃ | F | H | O | CH | 1.5732 (25.5) |
| (9) | F | H | —C≡CH | —CH₃ | F | H | O | CH | 1.5584 (24.0) |
| (10) | Cl | H | —C≡CH | —CH₃ | F | H | O | CH | 1.5663 (25.0) |
| (11) | —OC₂H₅ | Cl | —C≡CH | —CH₃ | F | H | O | CH | 1.5670 (24.0) |
| (12) | —OCH₂O— | | —C≡CH | —CH₃ | F | H | O | CH | 1.5801 (24.5) |
| (13) | —CF₃ | H | —C≡CH | —CH₃ | H | H | O | CH | 1.5392 (24.0) |
| (14) | —OCH₂O— | | —C≡CH | —CH₃ | H | H | O | CH | 1.5965 (20.0) |
| (15) | —OC₂H₅ | H | —C≡CH | —CH₃ | H | F | O | CH | 1.5594 (25.0) |
| (16) | —OC₂H₅ | Cl | —C≡CH | —CH₃ | H | H | O | CH | 1.5732 (24.5) |
| (17) | —OCHF₂ | H | —C≡CH | —CH₃ | H | H | O | CH | 1.5530 (22.0) |
| (18) | —OC₂H₅ | H | —C≡CH | —CH₃ | H | H | O | N | 1.5821 (19.0) |
| (19) | —OC₂H₅ | H | —CH=CH₂ | —CH₃ | H | H | O | N | 1.5884 (20.0) |
| (20) | —OC₂H₅ | H | —C≡CH | —CH₃ | F | H | O | N | 1.5740 (21.0) |
| (21) | —OC₂H₅ | H | —C≡CH | —CH₃ | F | H | NH | CH | 1.5890 (20.5) |
| (22) | —OC₂H₅ | H | —C≡CH | —CH₃ | H | H | S | CH | 1.6081 (24.0) |
| (23) | —C₂H₅ | H | —C≡CH | —CH₃ | H | H | O | CH | 1.5709 (26.5) |
| (24) | —OCH₃ | H | —C≡CH | —CH₃ | H | H | O | CH | 1.5839 (26.5) |
| (25) | Cl | H | —C≡CH | —CH₃ | H | H | O | CH | 1.5822 (27.0) |
| (26) | Cl | H | —C≡CH | —C₂H₅ | H | H | O | CH | 1.5731 (27.0) |
| (27) | —OCHF₂ | Cl | —C≡CH | —CH₃ | F | H | O | CH | 1.5462 (23.0) |
| (28) | —OC₂H₅ | H | —C≡CH | H | H | H | O | CH | 1.5776 (22.5) |
| (29) | —OC₂H₅ | H | —C≡CH | —C₂H₅ | F | H | O | CH | 1.5613 (21.5) |
| (30) | —OC₂H₅ | H | —C≡CH | —CH₃ | F | H | CH₂ | CH | 1.5621 (20.5) |
| (31) | —OC₂H₅ | H | —CH=CH₂ | —CH₃ | F | H | NH | CH | 1.5751 (21.5) |
| (32) | —OC₂H₅ | H | —C≡CH | —C₂H₅ | H | H | O | CH | 1.5736 (20.5) |
| (33) | —OC₂H₅ | H | —C≡CH | —CH₃ | F | —CH₃ | O | CH | 1.5628 (22.0) |
| (34) | —OC₂H₅ | H | —C≡CH | —CH₃ | F | Cl | O | CH | 1.5644 (23.5) |
| (35) | F | H | —C≡CH | —CH₃ | H | H | O | CH | 1.5602 (24.5) |
| (36) | Cl | Cl | —C≡CH | —CH₃ | F | H | O | CH | 1.5698 (24.0) |
| (37) | —CF₃ | H | —C≡CH | —CH₃ | F | H | O | CH | 1.5403 (28.0) |
| (38) | —OC₂H₅ | H | —C≡CH | —CH₃ | F | F | O | CH | 1.5506 (24.0) |
| (39) | —C₂H₅ | H | —C≡CH | CH₃ | F | H | O | CH | 1.5618 (25.0) |
| (40) | —OCH₂CH=CH₂ | Cl | —C≡CH | CH₃ | F | H | O | CH | 1.5687 (27.5) |
| (41) | Cl | H | —C≡CH | —C₂H₅ | F | H' | O | CH | 1.5672 (27.0) |
| (42) | —OC₂H₅ | H | —C≡CH | —nC₄H₉ | F | H | O | CH | 1.5649 (28.0) |
| (43) | —OC₂H₅ | H | —C≡CH | H | F | H | O | CH | 1.5688 (22.0) |
| (44) | —OCH₃ | H | —C≡CH | —CH₃ | H | H | O | N | 1.5816 (18.5) |

*Specific examples of the substituents $R_1, R_2, R_3, R_4, R_5, R_6$, Y and Z, of the compound represented by the general formula (I)

REFERENCE EXAMPLE 1

To a solution of 8.8 g of diisopropylamine in 150 ml of dry tetrahydrofuran were added 50 ml (1.5 mmole/ml) of n-butyl lithium at −50° C. After stirring at −20° C. for 30 minutes, 10.0 g of 4-ethoxyphenylacetonitrile was added thereto at −50° C. After stirring at the same temperature for 1 hour, 10.1 g of methyl iodide was added dropwise at −50° C. After stirring at the same temperature for 3 hours and then at 20° C. for 10 hours, the reaction solution was poured into 10% aqueous hydrochloric acid and extracted with ethyl acetate. After concentrating the ethyl acetate layer, the residual oil was column-chromatographed on silica gel (developing solvent, n-hexane: ethyl acetate=20:1) to obtain 9.50 g of the desired 2-(4-ethoxyphenyl) propionitrile [corresponding to the compound represented by the foregoing formula (II) wherein $R_1$ is an ethoxy group, $R_2$ is a hydrogen atom and $R_4$ is a methyl group] as a pale yellow oil.

Yield; 87.4%

NMR data (in $CDCl_3$)

$\delta$(ppm) 1.40(t,3H), 1.63(d,3H), 3.87(q,1H), 4.03(q,2H), 7.1(q,4H)

REFERENCE EXAMPLE 2

To a mixture of 2.01 g of sodium hydride (60% oil dispersion) and 100 ml of dry dimethylformamide were added dropwise at 40° C. 8.0 g of 2-(4-ethoxyphenyl)-propionitrile obtained above. After dropwise addition, the mixture was stirred at the same temperature for 30 minutes, and 15.2 g of 3-(3-phenoxyphenyl)propyl bromide were added dropwise thereto at 20° C. After dropwise addition, the reaction solution was stirred at 20° C. for 12 hours, poured into 5% aqueous hydrochloric acid, and then extracted with ethyl acetate. The ethyl acetate layer was washed with an aqueous sodium chloride solution and dried over anhydrous magnesium sulfate. After concentrating the solvent, the residual oil was column-chromatographed on silica gel (developing solvent, n-hexane: ethyl acetate=15:1) to obtain 15.6 g of the desired 2-(4-ethoxyphenyl)-2-methyl-5-(3phenoxyphenyl) pentanonitrile [corresponding to the compound represented by the foregoing general formula (IV) wherein $R_1$ is an ethoxy group, $R_2$, $R_5$ and $R_6$ are a hydrogen atom, $R_4$ is a methyl group and Y is an oxygen atom].

Yield: 88.6%

NMR (in CDCl3): $\delta$(ppm) 1.40(t,3H), 1.63(s,3H), 1.7-2.0(m,4H), 2.57(bt,2H), 4.0,(q,2H), 6.8-7.5(m,13H)

REFERENCE EXAMPLE 3

To a solution of 15.6 g of the nitrile obtained in Reference example 2 in 150 ml of dry toluene were added dropwise at 0° C. 50 ml of an n-hexane solution of diisobutylaluminum hydride, and the mixture was stirred at 20° C. for 12 hours. The reaction solution was poured into 150 ml of ice water containing 30 ml of concentrated hydrochloric acid and stirred for 2 hours. The toluene layer was separated, washed with an aqueous sodium chloride solution, dried over anhydrous magnesium sulfate and then concentrated. The solvent still present in the residual oil was completely distilled off under reduced pressure to obtain 15.7 g of a crude 2-(4-ethoxyphenyl)-2-methyl-5-(3-phenoxyphenyl)pentylaldehyde [corresponding to the aldehyde compound represented by the foregoing general formula (V) wherein $R_1$ is an ethoxy group, $R_2$, $R_5$ and $R_6$ are a hydrogen atom, $R_4$ is a methyl group and Y is an oxygen atom]as a pale yellow oil.

Crude yield: 100%

NMR (in $CDCl_3$): $\delta$(ppm) 1.38(s,3H), 1.39(t,3H), 1.7-2.0(m,4H), 2.55(bt,2H), 4.0(q,2H), 6.8-7.4(m,13H), 9.40(s,1H)

REFERENCE EXAMPLE 4

To a solution of 740 mg of methyltriphenylphosphonium bromide in 15 ml of dry tetrahydrofuran were added dropwise 1.4 ml (1.4 mmole/ml) of n-butyl lithium at −40° C. under a nitrogen stream. After dropwise addition, stirring was continued at the same temperature for 1 hour. Thereafter, 400 mg of the crude aldehyde obtained in Reference example 3 were added dropwise at −50° C., and the mixture was stirred at same temperature for 2 hours and then at 0° C. for further 12 hours. After adding 20 ml of n-hexane to the reaction solution, the solution was filtered, and the filtrate was concentrated. The residue was column-chromatographed on silica gel (developing solvent, n-hexane: ethyl acetate=20:1) to obtain 345 mg of the desired 3-(4-ethoxyphenyl)-3-methyl-6-(3-phenoxyphenyl)-1-hexene [Compound No. (1)] as a pale yellow oil.

Yield; 86.7%

NMR (in $CDCl_3$):

$\delta$(ppm) 1.34(s,3H), 1.42(t,3H), 1.6-1.8(m,4H), 2.58(bt,2H), 4.05(q,2H), 4.9-5.2(m,2H), 5.8-6.3(m,1H), 6.7-7.4(13H)

REFERENCE EXAMPLE 5

2.0 Grams of the aldehyde obtained in Reference example 3 and 5.4 g of triphenylphosphine were dissolved in 30 ml of dichloromethane, and 3.4 g of carbon tetrabromide were added thereto at −30° C. under a nitrogen stream. The mixture was stirred at 20° C. for 12 hours. After adding 50 ml of n-hexane to the reaction solution, the solution was filtered through Celite, and the filtrate was concentrated. The residue obtained was column-chromatographed on silica gel (developing solvent, n-hexane:ethyl acetate=20:1) to obtain 2.7 g of 1,1-dibromo-3-(4-ethoxyphenyl)-3-methyl-6-(3-phenoxyphenyl)-1-hexene.

Yield: 96.3%

NMR (in $CDCl_3$): $\delta$(ppm) 1.39(t,3H), 1.47(s,3H), 1.6-2.0(m,4H), 2.50(bt,2H), 4.0(1,2H), 6.7-7.4(m,14H)

1.92 Grams of the dibromide obtained above were dissolved in 20 ml of dry tetrahydrofuran, and n-butyl lithium of 2.2 times by mole was added dropwise at −40° C. under a nitrogen stream. After stirring at the same temperature for 1 hour and then at 20° C. for further 2 hours, the reaction solution was poured into 5% aqueous hydrochloric acid and extracted with ethyl acetate. The ethyl acetate layer was washed with an aqueous sodium chloride solution and dried over anhydrous magnesium sulfate, and the solvent was removed by evaporation. The residual oil was column-chromatographed on silica gel (developing solvent, n-hexane: ethyl acetate=20:1) to obtain 1.21 g of the desired 3-(4-ethoxyphenyl)-3-methyl-6-(3-phenoxyphenyl)-1-hexyne [Compound no. (3)]as a pale yellow oil.

NMR (in $CDCl_3$) $\delta$(ppm) 1.39(t,3H), 1.53(s,3H), 1.7-2.0(m,4H), 2.33(s,1H), 2.52(bt,2H), 4.0(q,2H), 6.7-7.4(13H)

REFERENCE EXAMPLE 6

Under a nitrogen atmosphere, 0.53 g of sodium hydride (60% oil dispersion) was added to 20 ml of dry dimethylformamide, and 2.77 g of trimethylphosphonoacetate were added dropwise over 5 minutes with ice-cooling. After dropwise addition, stirring was continued at room temperature for 30 minutes. A solution of 2.02 g of 2-formyl-6-phenoxypyridine in 5 ml of dry dimethylformamide was added dropwise thereto over 5 minutes with ice-cooling. After dropwise addition, stirring was continued at room temperature for 14 hours. The reaction solution was poured into ice water, neutralized to a pH of 6.8 with aqueous dilute hydrochloric acid, and then extracted twice with diethyl ether. The ether layers were combined, washed with a saturated aqueous sodium chloride solution and dried over anhydrous magnesium sulfate. The solvent was then removed by evaporation under reduced pressure, and the residue was column-chromatographed on silica gel (developing solvent, n-hexane:ethyl acetate=7.1) to obtain 2.1 g of the desired methyl 3-(6-phenoxypyridin-2-yl)propenate.

After dissolving 2.1 g of the resulting compound in 100 ml of ethyl acetate, 400 mg of 5% palladium-carbon powder were added thereto, and catalytic hydrogenation was carried out at room temperature and atmospheric pressure.

After confirming that the absorption of hydrogen gas stopped, the catalyst was removed by filtration. The filtrate was concentrated under reduced pressure to obtain 2.0 g of methyl 3-(6-phenoxypyridin-2-yl)propionate [corresponding to the compound represented by the foregoing general formula (VIII) wherein $R_5$ and $R_6$ are a hydrogen atom and $R_7$ is a methyl group].

NMR (solvent, deutero chloroform; internal standard, TMS): $\delta$(ppm) 2.53–3.20(m,4H), 3.60(s,3H), 6.50–7.62(m,8H)

REFERENCE EXAMPLE 7

Under a nitrogen atmosphere, 235 mg of sodium hydride (60% oil dispersion) were added to 50 ml of dry tetrahydrofuran, and the mixture was heated to 50° C. to 60° C. A solution of 864 mg of 4-methoxyphenylacetonitrile and 1.51 g of methyl 3-(6-phenoxypyridin-2-yl)propionate in 10 ml of dry tetrahydrofuran were added dropwise thereto over 5 minutes. After dropwise addition, the reaction solution was heated under reflux for 2 hours, cooled with ice, poured into ice water, neutralized to a pH of 7 with aqueous dilute hydrochloric acid and extracted twice with ethyl acetate. The ethyl acetate layers were combined and dried over anhydrous magnesium sulfate, and the solvent was removed by evaporation under reduced pressure. The residue crystallized, so that the crystal was washed with a little diethyl ether, filtered and dried to obtain 0.91 g of the desired 2-(4-methoxyphenyl)-3-oxo-5-(6-phenoxypyridin-2-yl)valeronitrile [corresponding to the compound represented by the foregoing general formula (X) wherein $R_1$ is a methoxy group, $R_2$, $R_5$ and $R_6$ are a hydrogen atom] as a crystal.

m.p.: 122.5° C. (uncorrected)

NMR (solvent, deutero chloroform; internal standard, TMS): $\delta$(ppm) 3.09(bs,4H), 3.81(bs,4H), 6.71–7.82(m,12H)

REFERENCE EXAMPLE 8

0.91 Gram of the crystalline valeronitrile compound obtained in Reference example 7 was dissolved in 30 ml of tetrahydrofuran, and stirring was continued at room temperature for 4 hours in total, during which 93 mg of sodium borohydride were added thereto in four portions. The reaction solution was poured into ice water, neutralized to a pH of 7 with aqueous dilute hydrochloric acid and then extracted twice with ethyl acetate. The ethyl acetate layers were combined and dried over anhydrous magnesium sulfate. The solvent was then removed by evaporation under reduced pressure to obtain 0.88 g of a colorless oily product as residue. This product was 3-hydroxy-2-(4-methoxyphenyl)-5-(6-phenoxypyridin-2-yl)valeronitrile [corresponding to the compound represented by the foregoing general formula (XI) wherein $R_1$ is a methoxy group and $R_2$, $R_5$ and $R_6$ are a hydrogen atom].

NMR (solvent, deutero chloroform; internal standard, TMS): $\delta$(ppm) 2.83(bt,2H), 3.80(s,3H), 6.60–7.70(m,12H)

REFERENCE EXAMPLE 9

0.87 Gram of the nitrile compound obtained in Reference example 8 was dissolved in 40 ml of dry dimethoxyethane and cooled with ice. Thereafter, 2 ml of 1,8-diazabicyclo[5.4.0]undec-7-ene (DBU) were added, and then 1 ml of methanesulfonyl chloride was added dropwise over 1 minute. After dropwise addition, stirring was continued for 2 hours with ice-cooling. The reaction solution was poured into ice water, neutralized to a pH of 7 with aqueous dilute hydrochloric acid and extracted twice with diethyl ether.

The ether layers were combined, washed with a saturated aqueous sodium chloride solution and dried over anhydrous magnesium sulfate. The solvent was then removed by evaporation under reduced pressure, and the residue was column-chromtographed on silica gel (developing solvent, n-hexane:ethyl acetate=3:1) to obtain 0.35 g of the desired 2-(4-methoxyphenyl)-5-(6-phenoxypyridin-2-yl)-2-pentenonitrile [corresponding to the compound represented by the foregoing general formula (XII) wherein $R_1$ is a methoxy group, and $R_2$, $R_5$ and $R_6$ are a hydrogen atom].

NMR (solvent, deutero chloroform; internal standard, TMS): $\delta$(ppm) 2.65–3.00(m,4H), 3.80(s,3H), 6.52–7.75(M,13H)

REFERENCE EXAMPLE 10

0.3 Gram of the nitrile compound obtained in Reference example 9 was dissolved in 10 ml of ethyl acetate, and to this solution were added 100 mg of 5% palladium-carbon powder. Catalytic hydrogenation was then carried out at room temperature under atmospheric pressure. After confirming that the absorption of hydrogen gas stopped, the catalyst was removed by filtration. The filtrate was concentrated under reduced pressure to obtain 300 mg of the desired 2-(4-methoxyphenyl)-5-(6-phenoxypyridin-2-yl)valeronitrile [corresponding to the compound represented by the foregoing general formula (XIII) wherein $R_1$ is a methoxy group and $R_2$, $R_5$ and $R_6$ are a hydrogen atom].

NMR (solvent, deutero chloroform; internal standard, TMS): $\delta$(ppm) 1.70–2.08(m,4H), 2.50–2.88(bt,2H), 3.77(s,3H), 6.53–7.68(m,12H)

REFERENCE EXAMPLE 11

Under a nitrogen atmosphere, 34 mg of sodium hydride (60% oil dispersion) were suspended in 10 ml of dry dimethylformamide. A solution of 300 mg of the nitrile compound obtained in Reference example 10 and 120 mg of methyl iodide in 10 ml of dry dimethylformamide were added dropwise to this suspension at room temperature. After the dropwise addition, reaction was continued by heating the reaction solution to 50° C. to 60° C. for 1 hour and then maintaining it at room temperature for 12 hours. The reaction solution was poured into ice water, neutralized to a pH of 7 with aqueous dilute hydrochloric acid and then extracted twice with diethyl ether. The ether layers were combined and dried over anhydrous magnesium sulfate, and the solvent was removed by evaporation under reduced pressure. The residue obtained was column-chromatographed on silica gel (developing solvent, n-hexane:ethyl acetate=5:1) to obtain 288 mg of the desired 2-(4-methoxyphenyl)-2-methyl-5-(6-phenoxypyridin-2-yl)valeronitrile [corresponding to the compound represented by the foregoing general formula (XV) wherein $R_1$ is a methoxy group, $R_4$ is a methyl group, and $R_2$, $R_5$ and $R_6$ are a hydrogen atom].

NMR (solvent, deutero chloroform; internal standard, TMS): δ(ppm) 1.64(s,3H), 1.60-2.10(m,4H), 2.50-2.90(bt,2H), 3.80(s,3H), 6.58-7.70(m,12H)

REFERENCE EXAMPLE 12

Under a nitrogen atmosphere, 288 mg of the nitrile compound obtained in Reference example 11 were dissolved in 10 ml of dry toluene. Thereafter, 0.62 ml of a toluene solution (1.5 M solution) of diisobutylaluminum hydride (DIBAL) was added with ice-cooling, and the mixture was stirred at the same temperature for 2 hours. The reaction was traced by thin layer chromatography (TLC) to find the remainder of the material, so that 0.5 ml of the toluene solution (1.5 M solution) of DIBAL was additionally added, and reaction was continued at the same temperature for 1 hour and then at room temperature for 3 hours. The reaction solution was cooled with ice, 20 ml of cold aqueous dilute hydrochloric acid was added thereto, and stirring was continued at the same temperature for 3 hours. The reaction solution was separated, and the aqueous layer was extracted twice with ethyl acetate. The organic layers were combined, washed twice with a saturated aqueous sodium chloride solution and dried over anhydrous magnesium sulfate. The solvent was then removed by evaporation under reduced pressure to obtain 213 mg of the desired 2-(4-methoxyphenyl)-2-methyl-5-(6-phenoxypyridin-2-yl)pentanal.

NMR (solvent, deutero chloroform; internal standard, TMS): δ(ppm) 1.40(s,3H), 1.67-2.05(m,4H), 2.60-2.84(bt,3H), 3.80(s,3H), 6.58-7.70(m,12H), 9.45(s,1H)

REFERENCE EXAMPLE 13

Under a nitrogen atmosphere, 893 mg of triphenylphosphine and 213 mg of the aldehyde compound obtained in Reference example 12 were dissolved in 20 ml of dry dichloromethane. After cooling this solution to −50° C., 566 mg of carbon tetrabromide were added, and the solution was stirred at the same temperature for 2 hours. Thereafter, the temperature of the reaction solution was gradually raised to room temperature over 1 hours, and stirring was continued at room temperature for further 24 hours. After cooling the reaction solution with ice, 20 ml of cold methanol and then 30 ml of cold water were added, and stirring was continued for 10 minutes. The pH of the aqueous layer was adjusted to 8 with an aqueous dilute sodium hydroxide solution, and the layer was extracted with two 100-ml portions of diethyl ether. The organic layer was washed with a saturated aqueous sodium chloride solution, and the solvent was removed by evaporation under reduced pressure. After adding 50 ml of n-hexane to the residue and through stirring, the insoluble matter was removed by filtration, and the filtrate was concentrated under reduced pressure. To the residue obtained were added again 30 ml of n-hexane, and the mixture was well mixed and filtered to remove the insoluble matter. The filtrate was concentrated under reduced pressure. To the residue obtained were added again 20 ml of n-hexane, and the mixture was well mixed and filtered to remove the insoluble matter. The filtrate was concentrated under reduced pressure, and the residue obtained was column-chromatographed on silica gel (developing solvent, n-hexane:ethyl acetate=20:1) to obtain 128 mg of the desired 1,1-dibromo-3-(4-methoxyphenyl)-3-methyl-6-(6-phenoxypyridin-2-yl)-1-hexene.

NMR (solvent, deutero chloroform; internal standard, TMS): δ(ppm) 1.50(s,3H), 2.50-2.75(bt,2H), 3.78(s,3H), 6.60-7.75(m,13H)

REFERENCE EXAMPLE 14

Under a nitrogen atmosphere, 128 mg of the hexene compound obtained in Reference example 13 were dissolved in 15 ml of dry tetrahydrofuran, and the resulting solution was cooled to −50° C. Thereafter, 0.37 ml of a hexane solution (1.45 mole solution) of n-butyl lithium was added thereto, and reaction was carried out at the same temperature for 1 hour. The temperature of the reaction solution was raised to −10° C. over 30 minutes, and stirring was continued at the same temperature for further 30 minutes. The reaction solution was poured into cold aqueous dilute hydrochloric acid, shaken several times, neutralized to a pH of 8 with an aqueous dilute sodium hydroxide solution and extracted twice with diethyl ether. The ether layer was washed with a saturated aqueous sodium chloride solution and dried over anhydrous magnesium sulfate. The solvent was then removed by evaporation under reduced pressure, and the residue was column-chromatographed on silica gel (developing solvent, n-hexane:ethyl acetate=20:1) to obtain 54 mg of the desired 3-(4-methoxyphenyl)-3-methyl-6-(6-phenoxypyridin-2-yl)-1-hexyne [Compound No. (44)].

NMR (solvent, deutero chloroform; internal standard, TMS): δ(ppm) 1.51(s,3H), 2.32(s,1H), 2.44-2.76(bt,2H), 3.78(s,3H), 6.43-7.63(m,12H)

REFERENCE EXAMPLE 15

Under a nitrogen atmosphere, 2.0 g of 1,1-dibromo-3-(4-methoxyphenyl)-3-methyl-6-(6-phenoxypyridin-2-yl)-1-hexene were dissolved in 50 ml of dry acetonitrile, and 1.69 g of sodium iodide and 1.23 g of trimethylsilyl chloride were added thereto. The mixture was then heated under reflux for 6 hours. The reaction solution was poured into ice water and extracted twice with ethyl acetate. The ethyl acetate layer was successively washed with an aqueous dilute sodium sulfite solution and a saturated aqueous sodium chloride solution. The solvent was then removed by evaporation under reduced pressure to obtain 1.81 g of the desired 1,1- dibromo-3-(4-hydroxyphenyl)-3-methyl-6-(6-phenoxypyridin-2-yl)-1-hexene.

NMR (solvent, deutero chloroform; internal standard, TMS): δ(ppm) 1.51(s,3H), 2.56–2.88(bt,2H), 5.75–6.10(b,1H), 6.60–7.76(m,13H)

REFERENCE EXAMPLE 16

Under a nitrogen atmosphere, 1.8 g of the hexene compound obtained in Reference example 15 were dissolved in 50 ml of dry tetrahydrofuran, and cooled to −50° C. To this solution were added 7.5 ml of a hexane solution (1.4 mole solution) of n-butyl lithium, and the mixture was treated in the same manner as in Reference example 14. The residue obtained was column-chromatographed on silica gel (developing solvent, n-hexane:ethyl acetate=4:1) to obtain 990 mg of the desired 3-(4-hydroxyphenyl)-3-methyl-6-(6-phenoxypyridin-2-yl)-1-hexyne.

NMR (solvent, deutero chloroform; internal standard, TMS): δ(ppm) 1.51(s,3H), 2.30(s,1H), 2.42–2.72(bt,2H), 5.55–5.95(b,1H), 6.44–7.58(m,12H)

REFERENCE EXAMPLE 17

Under a nitrogen atmosphere, 111 mg of sodium hydride (60% oil dispersion) were suspended in 20 ml of dry dimethylformamide, and cooled to 0° C. To this solution was added dropwise a solution of 990 mg of the hexyne compound obtained in Reference example 16 in 5 ml of dry dimethylformamide. After the dropwise addition, the temperature of the reaction solution was raised to room temperature, and stirring was continued at the same temperature for 30 minutes. Thereafter, a solution of 360 mg of ethyl bromide in 3 ml of dry dimethylformamide was added, and stirring was continued at room temperature for 12 hours and then at 50° C. for another hour. The reaction solution was cooled, poured into ice-containing cold aqueous dilute hydrochloric acid, shaken thoroughly neutralized to a pH of 8 with an aqueous dilute sodium hydroxide solution and extracted twice with diethyl ether. The ether layers were combined and washed with a saturated aqueous sodium chloride solution. The solvent was then removed by evaporation under reduced pressure, and the residue was column-chromatographed on silica gel (developing solvent, n-hexane:ethyl acetate=20:1) to obtain 890 mg of the desired 3-(4-ethoxyphenyl)-3-methyl-6-(6-phenoxypyridin-2-yl)-1-hexyne [Compound No. (18)].

NMR (solvent, deutero chloroform; internal standard, TMS): δ(ppm) 1.39(t,3H), 1.51(2,3H), 2.29(s,1H), 2.45–2.72(bt,2H), 4.01(q,2H), 6.45–7.59(m,12H)

REFERENCE EXAMPLE 18

Under a nitrogen atmosphere, 4.39 g of 1,1-dibromo-3-(4-methoxyphenyl)-3-methyl-6-(3-phenoxyphenyl)-1-hexene (obtained by using 4-methoxyphenylacetonitrile in place of 4-ethoxyphenylacetonitrile in Reference example 1 and carrying out the same procedures as in Reference examples 2, 3 and 5) were dissolved in 20 ml of dry acetonitrile. To this solution were added 3.73 g of sodium iodide and 2.69 g of trimethylsilyl chloride at room temperature, and the mixture was heated under reflux for 6 hours with stirring. The reaction solution was poured into ice water and extracted twice with diethyl ether. The ether layers were combined, washed successively with an aqueous dilute sodium sulfite solution and a saturated aqueous sodium chloride solution, and dried over anhydrous magnesium sulfate. The solvent was removed by evaporation under reduced pressure to obtain 4.05 g of the desired 1,1-dibromo-3-(4-hydroxyphenyl)-3-methyl-6-(3-phenoxyphenyl)-1-hexene.

NMR (solvent, deutero chloroform; internal standard, TMS): δ(ppm) 1.48(s,3H), 2,32–2.65(bt,2H), 5.35–5.68(b,1H), 6.60–7.51(m,14H)

REFERENCE EXAMPLE 19

Under a nitrogen atmosphere, 4.05 g of the hexene compound obtained in Reference example 18 were dissolved in 40 ml of dry tetrahydrofuran and cooled to −50° C. To this solution were added 16.8 ml of a hexane solution of n-butyl lithium (1.46 M solution), and stirring was continued at the same temperature for 3 hours. The temperature of the reaction solution was gradually raised to −10° C., and the solution was stirred at the same temperature for further 10 minutes, poured into cold aqueous dilute hydrochloric acid and extracted twice with diethyl ether. The ether layers were combined, washed twice with a saturated aqueous sodium chloride solution and dried over anhydrous magnesium sulfate. The solvent was then removed by evaporation under reduced pressure to obtain 2.51 of the desired 3-(4-hydroxyphenyl)-3-methyl-6-(3-phenoxyphenyl)-1-hexyne.

NMR (solvent, deutero chloroform; internal standard, TMS): δ(ppm) 1.52(s,3H), 2.32(s,1H), 2.35–2.70(bt,2H), 5.15–5.90(b,1H), 6.56–7.48(m,13H)

REFERENCE EXAMPLE 20

Under a nitrogen atmosphere, 51 mg of sodium hydride (60% oil dispersion) were suspended in 10 ml of dry dimethylformamide, and a solution of 500 mg of the hexyne compound obtained in Reference example 19 in 2 ml of dry dimethylformamide was added thereto with ice-cooling. After stirring at room temperature for 1 hour, 129 mg of allyl chloride were added with ice cooling, and reaction was continued at room temperature for 14 hours. The reaction solution was poured into cold aqueous dilute hydrochloric acid and extracted twice with diethyl ether. The ether layers were combined, washed with a saturated aqueous sodium chloride solution and dried over anhydrous magnesium sulfate. The solvent was then removed by evaporation under reduced pressure, and the residue was column-chromatographed on silica gel(developing solvent, n-hexane:ethyl acetate=30:1) to obtain 390 mg of the desired 3-(4-allyloxyphenyl)-3-methyl-6-(3-phenoxyphenyl)-1-hexyne [Compound No. (7)].

NMR (solvent, deutero chloroform; internal standard, TMS): δ(ppm) 1.52(s,3H), 2.34(s,1H), 2.35–2.70(bt,2H), 4.40–4.60(bd,2H) 5.10–6.40(m,3H), 6.70–7.55(m,13H)

REFERENCE EXAMPLE 21

Under a nitrogen atmosphere, 101 mg of sodium hydride (60% oil dispersion) were suspended in 50 ml of dry dimethylformamide, and a solution of 1.0 g of the hexyne compound obtained in Reference example 19 in 5 ml of dry dimethylformamide was added thereto with ice-cooling. After continuing stirring at room temperature for 30 minutes, a chloro-difluoromethane gas was introduced in the reaction system, during which the inner temperature was kept at 50° C. to 60° C. After passing the gas for 1 hour, the reaction solution was cooled, poured into cold aqueous dilute hydrochloric acid and extracted twice with diethyl ether. The ether layers were combined, washed with a saturated aqueous sodium chloride solution and dried over anhydrous magnesium sulfate. The solvent was then removed by evaporation under reduced pressure, and the residue was column-chromatographed on silica gel (developing solvent, n-hexane:ethyl acetate=30:1) to obtain 175 mg of the desired 3-(4-difluoromethoxyphenyl)-3-methyl-6-(3-phenoxyphenyl)-1-hexyne [Compound No. (17)].

NMR (solvent, deutero chloroform; internal standard, TMS): $\delta$(ppm) 1.52(s,3H), 2.38(s,1H), 2.35–2.75(bt,2H), 6.48(t,1H), 6.70–7.60(m,13H)

When the present compounds are used as an active ingredient for an insecticidal and acaricidal composition, they may be used as it is without adding any other ingredients. Generally, however, they are formulated into emulsifiable concentrates, wettable powders, dusts, granules, oil sprays, aerosols, heating fumigants (e.g. mosquito coils, electric mosquito mats), foggings, non-heating fumigants, poisonous baits, etc. by mixing with solid carriers, liquid carriers, gaseous carriers, surface active agents, other auxiliaries for formulation, baits, etc., or impregnating into bases such as mosquito coil carrier, mat, etc. The composition of the present invention may also contain other ingredients, for example, other compounds possessing pesticidal, for example, insecticidal, acaricidal, herbicidal or fungicidal properties.

These preparations contain 0.01 to 95% by weight of the present compound as an active ingredient.

The solid carrier includes for example fine powders or granules of kaolin clay, attapulgite clay, bentonite, terra alba, pyrophyllite, talc, diatomaceous earth, calcite, corn stalk powder, walnut shell powder, urea, ammonium sulfate, synthetic hydrated silicon dioxide and the like. The liquid carrier includes for example aliphatic hydrocarbons (e.g. kerosene, light mineral oils), aromatic hydrocarbons (e.g. toluene, xylene, methylnaphthalene), halogenated hydrocarbons (e.g. dichloroethane, trichloroethylene, carbon tetrachloride), alcohols (e.g. methanol, ethanol, isopropanol, ethylene glycol, cellosolve), ketones (e.g., acetone, methyl ethyl ketone, cyclohexanone, isophorone), ethers (e.g. diethyl ether, dioxane, tetrahydrofuran), esters (e.g. ethyl acetate), nitriles (e.g. acetonitrile, isobutyronitrile), acid amides (e.g. dimethylformamide, dimethylacetamide), dimethyl sulfoxide, vegetable oils (e.g. soybean oil, cotton seed oil) and the like. The gaseous carrier includes for example freon gas, LPG (liquefied petroleum gas), dimethyl ether and the like. The surface active agent used for emulsification, dispersion, wetting, etc. includes for example anionic surface active agents such as the salt of alkyl sulfates, alkyl(aryl) sulfonates, dialkyl sulfosuccinates, the salt of polyoxyethylene alkylaryl ether phosphoric acid ester, naphthalenesulfonic acid/formalin condensates, etc., and nonionic surface active agents such as polyoxyethylene alkyl ether, polyoxyethylene polyoxypropylene block copolymers, sorbitan fatty acid esters, polyoxyethylene sorbitan fatty acid esters, etc. The adjuvants for formulation such as sticking agents, dispersing agents, etc. includes for example lignosulfonates, alginates, polyvinyl alcohol, gum arabic, molasses, casein, gelatin, CMC (carboxymethyl cellulose), pine oil agar, etc. The stabilizer includes for example alkyl phosphates [e.g. PAP (isopropyl acid phosphate), TCP (tricresyl phosphate)], vegetable oils, epoxidized oil, the foregoing surface active agents, antioxidants (e.g. BHT, BHA), fatty acid salts (e.g.sodium oleate, calcium stearate), fatty acid esters (e.g. methyl oleate, methyl stearate) and the like.

Next, formulation examples will be shown. The present compounds are shown by Compound No. described in Table 1. Parts in the examples are by weight.

Formulation Example 1

0.2 Part of each of the present compounds (1) to (44), 2 parts of xylene and 97.8 parts of kerosene are mixed to obtain the oil spray of each compound.

FORMULATION EXAMPLE 2

10 Parts of each of the present compounds (1) to (44), 14 parts of polyoxyethylene styrylphenyl ether, 6 parts of calcium dodecylbenzenesulfonate and 70 parts of xylene are well mixed to obtain the emulsifiable concentrate of each compound.

FORMULATION EXAMPLE 3

20 Parts of the present compound (1), 10 parts of fenitrothion, 3 parts of calcium lignosulfonate, 2 parts of sodium lauryl sulfate and 65 parts of synthetic hydrated silicon dioxide are well pulverized and mixed together to obtain the wettable powder of the compound.

FORMULATION EXAMPLE 4

0.5 Part of the present compound (2), 0.3 part of the foregoing PAP, 89.2 parts of kaolin clay and 10 parts of talc are well pulverized and mixed together to obtain the dust of the compound.

FORMULATION EXAMPLE 5

5 Parts of the present compound (3), 1 part of synthetic hydrated silicon dioxide, 2 parts of calcium lignosulfonate, 30 parts of bentonite and 62 parts of kaolin clay are well pulverized and mixed thoroughly, kneaded well with water, granulated and then dried to obtain the granules of the compound.

FORMULATION EXAMPLE 6

0.05 Part of the present compound (4), 0.2 part of tetramethrin, 0.05 part of resmethrin, 7 parts of xylene and 32.7 parts of deodorized kerosene are well mixed into a solution. The solution is filled in an aerosol container, and after attaching a valve portion to the container, 60 parts of a propellant (liquefied petroleum gas) is charged therein through the valve under pressure to obtain the aerosol of the compound.

FORMULATION EXAMPLE 7

0.3 Gram of the present compound (5), and 0.3 g of the d-trans chrysanthemate of allethrin are dissolved in 20 ml of methanol. This solution and 99.5 g of a mosquito coil carrier, which is a 3:5:1 mixture of Tabu powder, Pyrethrum marc and wood powder, are uniformly mixed with stirring. After evaporating methanol, 150 ml of water is added to the residue, and the mixture is well kneaded, shaped and dried to obtain the mosquito coil of the compound.

These preparations are used as they are or as diluted solutions with water. Also, they may be applied in mixture with other insecticides, acaricides, nematocides, fungicides, herbicides, plant growth regulators, fertilizers, soil improvers and the like.

When the present compound is used as an insecticidal and acaricidal composition, its dosage rate is generally 5 to 500 g per 10 ares. When emulsifiable concentrates, wettable powders, etc. are used as aqueous dilute solutions, the application concentration of the compound is 10 to 1000 ppm. Dusts, granules, oil sprays, aerosols, etc. are used as they are without dilution.

Next, test examples will be shown. The present compounds are shown by Compound No. in Table 1, and compounds used as a control are shown by Compound symbol in Table 2.

Thereafter, the feed was added to respective cups and the number of emerged mosquitoes of the respective cups was counted when all the mosquitoes of no treatment group had emergeed to calculate the inhibitory ratios of the emergence.

The mortality and the inhibitory ratio of the emergence are shown according to the following three criteria:

TABLE 2

| Compound symbol | Structural formula | Remarks |
|---|---|---|
| (A) | [structure: phenyl-O-phenyl-CH2-C(CH3)2-phenyl-Cl] | A compound disclosed in Jap. Pat. Appln. Kokai (Laid-open) No. 201737/1983 |
| (B) | [structure with ether linkage] | A compound disclosed in Jap. Pat. Appln. Kokai (Laid-open) No. 72928/1982 |
| (C) | [structure: isobutylphenyl-OC(=O)NHCH3] | BPMC |
| (D) | $(CH_3O)_2P(=S)-SCHCOOC_2H_5$ with $CH_2COOC_2H_5$ | Malathion |
| (E) | $Cl$-phenyl($CH_3$)-$N=CH-N(CH_3)_2$ | Chlordimeform |

TEST EXAMPLE 1

The emulsifiable concentrates of the following present compounds obtained according to Formulation example 2 were each diluted with water so as to obtain respective aqueous solutions containing 3.5 ppm of said compounds, respectively. One hundred ml of thus diluted aqueous solutions were poured into respective polyethylene cups of 180 ml volume, and 20 of the last instar larvae of common mosquito (*Culex pipiens pallens*) were liberated thereto. After one day, the dead or alive of the larvae were examined.

mortality:
  A; 90% or more,
  B; less than 90% to 10%,
  C; less than 10%.
inhibitory:
  A; 90% or more,
ratio of emergence
  B; less than 90% to 80%
  C; less than 80%.
The results are shown in Table 3.

TABLE 3

| Test compound | Mortality | Inhibitory ratio of emergence | Test compound | Mortality | Inhibitory ratio of emergence | Test compound | Mortality | Inhibitory ratio of emergence |
|---|---|---|---|---|---|---|---|---|
| (1) | A | A | (16) | B | A | (31) | A | A |
| (2) | A | A | (17) | A | A | (32) | A | A |
| (3) | A | A | (18) | A | A | (33) | A | A |
| (4) | A | A | (19) | B | A | (34) | A | A |
| (5) | A | A | (20) | A | A | (35) | A | A |

TABLE 3-continued

| Test compound | Mortality | Inhibitory ratio of emergence | Test compound | Mortality | Inhibitory ratio of emergence | Test compound | Mortality | Inhibitory ratio of emergence |
|---|---|---|---|---|---|---|---|---|
| (6) | A | A | (21) | A | A | (36) | B | A |
| (7) | B | A | (22) | B | A | (37) | A | A |
| (8) | A | A | (23) | A | A | (38) | A | A |
| (9) | A | A | (24) | B | A | (39) | A | A |
| (10) | A | A | (25) | A | A | (40) | B | A |
| (11) | A | A | (26) | A | A | (41) | A | A |
| (12) | A | A | (27) | B | A | (42) | B | A |
| (13) | A | A | (28) | A | A | (43) | A | A |
| (14) | A | A | (29) | A | A | (44) | B | A |
| (15) | A | A | (30) | A | A | no treatment | C | C |

TEST EXAMPLE 2

The emulsifiable concentrates of the following present compounds obtained according to Formulation example 2 were each diluted with water to obtain respective 667 times dilution aqueous solutions (corresponding to 150 ppm) containing said compounds, respectively. Two ml of thus diluted solutions were impregnated into the artificial feeds (13 g) for tobacco cutworms (*Spodoptera litura*) and thus prepared feeds were placed in polyethylene cups of 11 cm in diameter, respectively. Ten of the 4th instar larvae were liberated thereon.

Six days after, the dead and alive of the larvae were examined to calculate the mortality (two replications). The results are shown in Table 4.

TABLE 4

| Test compound | Mortality (%) | Test compound | Mortality (%) |
|---|---|---|---|
| (1) | 100 | (25) | 100 |
| (2) | 100 | (29) | 100 |
| (3) | 100 | (30) | 100 |
| (4) | 100 | (31) | 100 |
| (5) | 100 | (33) | 100 |
| (6) | 100 | (34) | 100 |
| (7) | 100 | (35) | 100 |
| (8) | 100 | (37) | 100 |
| (9) | 100 | (38) | 100 |
| (10) | 100 | (39) | 100 |
| (11) | 100 | (42) | 100 |
| (12) | 100 | (43) | 100 |
| (13) | 100 | (44) | 100 |
| (14) | 100 | | |
| (15) | 100 | | |
| (16) | 100 | | |
| (17) | 100 | | |
| (18) | 100 | | |
| (20) | 100 | | |
| (21) | 100 | | |
| (22) | 100 | | |
| (23) | 100 | | |
| (24) | 100 | | |

TEST EXAMPLE 3

The emulsifiable concentrates of the following present compounds and control compounds obtained according to Formulation example 2 were each diluted with water to a prescribed concentration, and rice seedlings (about 12 cm in length) were dipped for 1 minute in the resulting aqueous dilute solutions. After air-drying, the seedlings were placed in test tube, and 10 adults of a resistant strain of green rice leafhopper (*Nephotetix cincticecs*) were liberated in the tube. After one day, the dead and alive of the adults were examined to obtain $LC_{50}$ (50% lethal concentration)(two replications).

The result is shown in Table 5.

TABLE 5

| Test compound | $LC_{50}$ value (ppm) | Test compound | $LC_{50}$ value (ppm) |
|---|---|---|---|
| (2) | 80 | (22) | 90 |
| (3) | 18 | (23) | 40 |
| (4) | 10 | (24) | 27 |
| (5) | 56 | (25) | 61 |
| (6) | 36 | (27) | 31 |
| (8) | 54 | (30) | 28 |
| (9) | 49 | (33) | 23 |
| (10) | 32 | (34) | 18 |
| (11) | 49 | (35) | 93 |
| (12) | 63 | (36) | 64 |
| (13) | 10 | (37) | 14 |
| (15) | 3.6 | (38) | 1.9 |
| (16) | 15 | (39) | 21 |
| (17) | 68 | (40) | 46 |
| (20) | 74 | (43) | 74 |
| (21) | 24 | | |
| | | (A) | ≈500 |
| | | (C) | 190 |
| | | (D) | ≈500 |

TEST EXAMPLE 4

The emulsifiable concentrates of the following present compounds and control compounds obtained according to Formulation example 2 were each diluted with water to a prescribed concentration, and the rice seedlings (about 12 cm in length) were dipped for 1 minute in the resulting aqueous dilute solutions. After air-drying, the seedlings were placed in a test tube, and 10 adults of brown rice planthopper (*Nilaparvata lugens*) were liberated in the tube. After one day, the dead and alive of the adults were examined to obtain $LC_{50}$ value (50% lethal concentration)(two replications).

The result is shown in Table 6.

TABLE 6

| Test compound | $LC_{50}$ value (ppm) |
|---|---|
| (3) | 34 |
| (4) | 24 |
| (20) | 25 |
| (21) | 15 |
| (A) | >500 |
| (B) | 110 |

TEST EXAMPLE 5

The emulsifiable concentrates of the following present compounds and control compounds obtained according to Formulation example 2 were each diluted with water to a prescribed concentration, and one ml each of thus prepared solutions was impregnated into the artificial feeds for rice stem borer (*Chilo suppressalis*)

which had been previously prepared in polyethylene cups of 5.5 cm in diameter, respectively. Ten of the larvae of the 10 days old were liberated thereon. The dead and alive larvae were examined to obtain $LC_{50}$ value (50% lethal concentration) (two replications).

TABLE 7

| Test compound | $LC_{50}$ value (ppm) |
|---|---|
| (3) | 3.6 |
| (4) | 1.9 |
| (6) | 1.9 |
| (9) | 4.2 |
| (11) | 2.3 |
| (17) | 3.6 |
| (21) | 1.5 |
| (34) | 4.2 |
| (A) | 230 |
| (B) | 7.4 |

TEST EXAMPLE 6

On the bottom of a polyethylene cup of 5.5 cm in diameter was placed a piece of filter paper of the same size as the bottom, and 0.7 ml of a test solution, prepared by diluting the emulsifiable concentrates of the following present compounds and control compounds prepared according to Formulation example 2 to a prescribed concentration with water, was added dropwise to the filter paper. Thirty milligrams of sucrose were uniformly placed on the filter paper as bait. Thereafter, 10 adult female houseflies (*Musca domestica*) of WHO strains were liberated in the cup, which was then covered with a lid. After 48 hours, the dead and alive were examined to obtain $LC_{50}$ value (50% lethal concentration) (two replications).

The result is shown in Table 8.

TABLE 8

| Test compound | $LC_{50}$ value (ppm) |
|---|---|
| (4) | 18 |
| (5) | 13 |
| (6) | 15 |
| (11) | 12 |
| (12) | 13 |
| (27) | 11 |
| (37) | 13 |
| (38) | 14 |
| (39) | 17 |
| (A) | ≈500 |
| (B) | 28 |

TEST EXAMPLE 7

The emulsifiable concentrates of the following compounds and control compounds obtained according to Formulation example 2 were each diluted with water one thousand times (corresponding to 100 ppm) and each of thus prepared solutions was sprayed at the rate of 20 ml/2 pots to the rice plant seedlings planted in Wagner pots having a surface area of one ten thousandth are. After air-drying, the threated plants were covered with the iron wire cages, and about 15 adults of brown rice planthoppers (*Nilaparavata lugens*) were liberated thereto. Further, about 15 adults thereof were also liberated thereto 4 days after the application to examine the residual effects. Twenty four hours after each liberation, the dead and alive adults were examined to calculate the mortality.

The results are shown in Table 9 below.

TABLE 9

| | Mortality (%) | |
|---|---|---|
| Test compound | liberated just after air-drying | liberated 4 days after application |
| (1) | 100 | 100 |
| (2) | 100 | 100 |
| (3) | 100 | 95 |
| (4) | 100 | 100 |
| (7) | 100 | 93 |
| (A) | 71 | 44 |
| (B) | 100 | 65 |
| (C) | 100 | 6 |
| no treatment | 0 | 3 |

TEST EXAMPLE 8

The female adults of carmine spider mite (*Tetranychus cinnabarinus*) were put at a rate of 10 adults/leaf on the leaves of potted kidney bean (at the primordial leaf stage) which had elapsed 7 days after sowing, and placed in a constant-temperature room kept at 25° C. After 6 days, the 200-fold aqueous dilute solutions (corresponding to 500 ppm), prepared from the emulsifiable concentrates of the following present compounds and control compounds prepared according to Formulation example 2, were each sprayed at a rate of 15 ml/pot on a turn table. At the same time, the soil in the pot was treated with 2 ml of each aqueous solution. After 8 days, the degree of damage of the plant by the mite was examined.

Criteria of the effect:
−: No damage is observed.
+: Slight damage is observed.
++: The same damage as in the untreated plot is observed.

The result is shown in Table 10.

TABLE 10

| Test compound | Degree of damage |
|---|---|
| (1) | − ~ + |
| (2) | − |
| (3) | − |
| (4) | − |
| (6) | − |
| (7) | − |
| (8) | − |
| (10) | − |
| (11) | − |
| (13) | − |
| (16) | − |
| (17) | − |
| (18) | − ~ + |
| (20) | − ~ + |
| (25) | − |
| (39) | − ~ + |
| (43) | − ~ + |
| (A) | + ~ ++ |
| (B) | + ~ ++ |
| (E) | − ~ + |
| no treatment | ++ |

TEST EXAMPLE 9

(Fish toxicity test)

Twenty liters of each of the aqueous solutions containing the prescribed concentrations of the present compounds and comparative control one, and 10 young carp were liberated thereto. Forty-eight hours after, the dead and alive carp were examined to obtain $LC_{50}$ value, (50% lethal concentration) according to Probit method. All the tests were carried out in thermostatic aquaria whose temperatures were kept at 25°±1° C. The results are shown in Table 11.

Tested fish:
young Japanese carp (*Cyprinida carpio*)
Average body length ±S.D.: 2.94±0.19 cm.
Average body weight ±S.D.: 0.65±0.13 g.

TABLE 11

| Test compound | LC$_{50}$ value (ppm) |
|---|---|
| (3) | >10 |
| (4) | >10 |
| (D) | 4.5 |

What is claimed is:

1. A compound represented by the general formula,

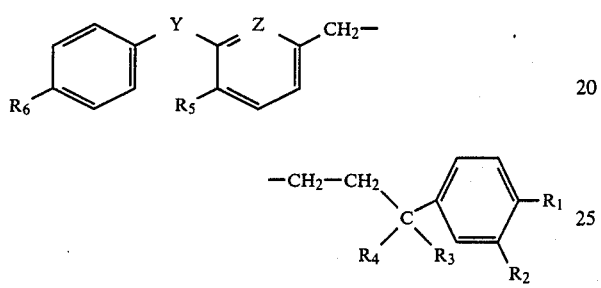

R$_1$ and R$_2$, which may be the same or different, are a hydrogen atom, a halogen atom, a lower alkyl group, a trifluoromethyl group, a lower alkoxyl group, a lower alkenyloxy group or a halogenated lower alkoxyl group, or are, taken together, a methylenedioxy group; R$_3$ is a vinyl group or a ethynyl group; R$_4$ is a hydrogen atom or a lower alkyl group; R$_5$ is a hydrogen atom or a fluorine atom; R$_6$ is a hydrogen atom, a halogen atom, a lower alkyl group, a lower alkoxyl group or a trifluoromethyl group; Z is a nitrogen atom or a group represented by the formula —CH=; when Z is a nitrogen atom, Y is an oxygen atom; and when Z is a group of the formula —CH=, Y is an oxygen atom, a sulfur atom, a methylene group or a group represented by the formula —NH—.

2. The compound according to claim 1, wherein R$_1$ and R$_2$, which may be the same or different, are a hydrogen atom, a halogen atom, a C$_{1-4}$ alkyl group, a trifluoromethyl group, a C$_{1-4}$ alkoxyl group, a C$_{2-4}$ alkenyloxy group or a halogenated C$_{1-4}$ alkoxyl group, or are, taken together, a methylenedioxy group; R$_4$ is a C$_{1-4}$ alkyl group; R$_6$ is a hydrogen atom, a halogen atom, a C$_{1-4}$ lower alkyl group, a C$_{1-4}$ alkoxyl group or a trifluoromethyl group; Z is a group represented by the formula —CH=; and Y is an oxygen atom or a group represented by the formula —NH—.

3. The compound according to claim 2, wherein R$_4$ is a methyl group.

4. The compound according to claim 2, wherein R$_3$ is an ethynyl group and R4 is a methyl group.

5. The compound according to claim 4, wherein R$_1$ is a halogen atom, a C$_2$-alkyl group, a trifluoromethyl group, a C$_{2-4}$ alkoxyl group, a C$_{2-4}$ alkenyloxy group or a fluorinated C$_{1-4}$ alkoxyl group; R2 is a hydrogen atom; R5 is a fluorine atom; R6 is a hydrogen atom or a halogen atom; and Y is a group represented by the formula —NH—.

6. The compound according to claim 4, wherein R is a halogen atom, a C$_{2-4}$ alkyl group, a trifluoromethyl group a C$_{2-4}$ alkoxyl group, a C$_{2-4}$ alklenyloxy group or a fluorinated C$_{2-4}$ alkoxyl group; R 2 is a hydrogen group; R$_6$ is a hydrogen atom or a halogen atom; and Y is an oxygen atom.

7. A compound of the formula

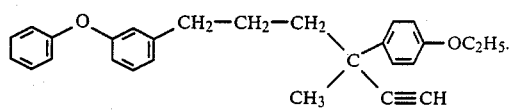

8. A compound of the formula,

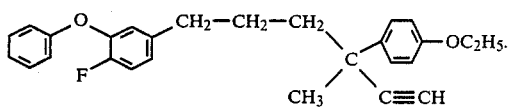

9. A compound of the formula,

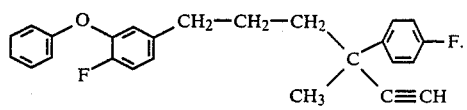

10. A compound of the formula,

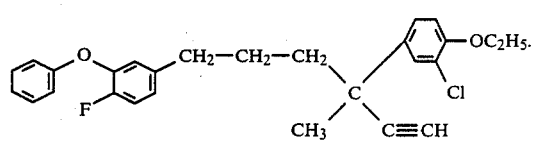

11. A compound of the formula,

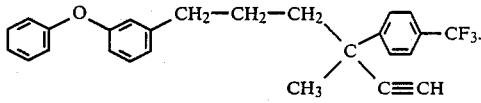

12. A compound of the formula,

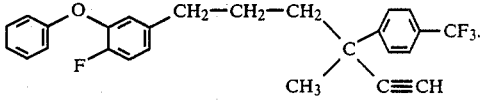

13. A compound of the formula,

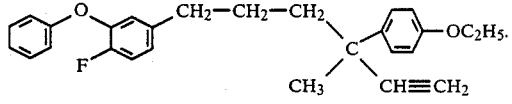

14. A compound of the formula,

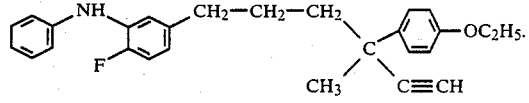

15. A compound of the formula,

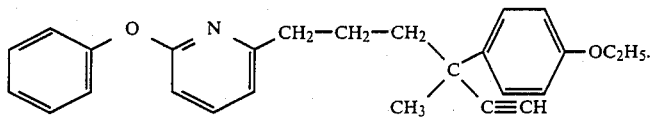

16. A compound of the formula,

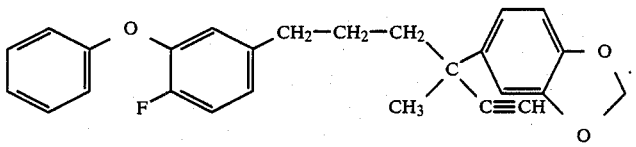

17. A compound of the formula,

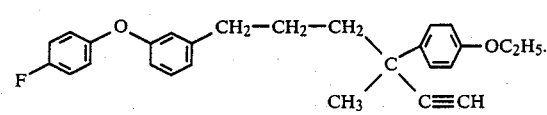

18. A compound of the formula,

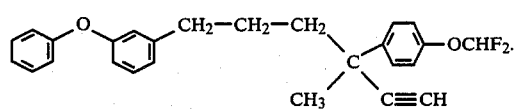

19. A compound of the formula,

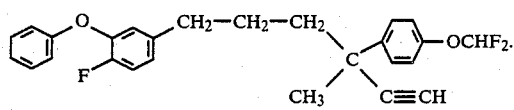

20. A compound of the formula,

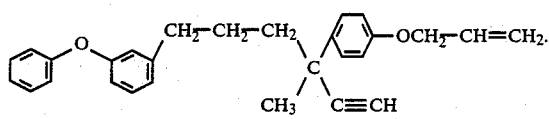

21. A compound of the formula,

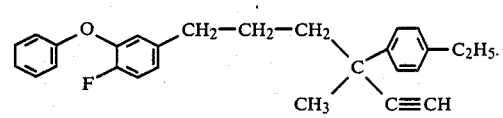

22. An insecticidal and acaricidal composition which comprises as an active ingredient an insecticidally and-/or an acaricidally effective amount of the compound as recited in claim 1 and an inert carrier.

23. An insecticidal and acaricidal composition which comprises as an active ingredient an insecticidally and-/or an acaricidally effective amount of the compound as recited in claim 3 and an inert carrier.

24. An insecticidal and acaricidal composition which comprises as an active ingredient an insecticidally and-/or an acaricidally effective amount of the compound as recited in claim 4 and an inert carrier.

25. An insecticidal and acaricidal composition which comprises as an active ingredient an insecticidally and-/or acaricidally effective amount of the compound as recited in claim 5 and an inert carrier.

26. An insecticidal and acaricidal composition which comprises as an active ingredient an insecticidally and-/or an acaricidally effective amount of the compound as recited in claim 6 and an inert carrier.

27. A method for controlling an insect and/or an acarid which comprises applying to said insect and/or acarid an insecticidally and/or acaricidally effective amount of the compound according to claim 1.

* * * * *